United States Patent [19]

Cozzi et al.

[11] 4,342,775
[45] Aug. 3, 1982

[54] 3-(1-IMIDAZOLYL)-DERIVATIVES OF 2,3-DIHYDRO-4H-1-BENZOPYRAN

[75] Inventors: Paolo Cozzi; Nicola Mongelli; Antonio Pillan, all of Milan; Maria Bergamaschi, Fiorenzuola d'Arda; Pier P. Lovisolo, Milan, all of Italy

[73] Assignee: Farmitalia Carlo Erba S.p.A., Milan, Italy

[21] Appl. No.: 233,961

[22] Filed: Feb. 12, 1981

[30] Foreign Application Priority Data

Mar. 4, 1980 [GB] United Kingdom ............... 8007336
Jan. 29, 1981 [GB] United Kingdom ............... 8102741

[51] Int. Cl.³ .................. C07D 405/04; A61K 31/33; A61K 31/415
[52] U.S. Cl. ................................ 424/273 R; 548/336
[58] Field of Search ................... 424/273 R; 548/336

[56] References Cited

U.S. PATENT DOCUMENTS 4,013,673  3/1977  Connor et al. .................. 546/268
4,116,971  9/1978  Strandtmann .................... 548/253
4,157,984  6/1979  Zilliken ......................... 252/407

FOREIGN PATENT DOCUMENTS 666541   3/1965  Belgium .
53-18573  2/1978  Japan .
53-18574  2/1978  Japan ........................... 548/253
53-18575  2/1978  Japan .
53-40775  4/1978  Japan .
54-59279 12/1979  Japan .

Primary Examiner—Jane T. Fan
Attorney, Agent, or Firm—Murray and Whisenhunt

[57] ABSTRACT 3-(1-imidazolyl)-derivatives of 2,3-dihydro-4H-1-benzopyran, such as, for instance, the compound 3-(1-imidazolyl)-2,3-dihydro-4H-1-benzopyran-4-one, are disclosed, as well as method of making same, and pharmaceutical compositions containing same. Also disclosed is a method of using such compounds to inhibit blood platelet aggregation, to increase total serum HDL cholesterol, to increase the ratio between α-lipoprotein and β-lipoprotein total cholesterol, and/or of reducing total serum cholesterol or serum triglycerides.

76 Claims, No Drawings

3-(1-IMIDAZOLYL)-DERIVATIVES OF 2,3-DIHYDRO-4H-1-BENZOPYRAN

The present invention relates to new N-imidazolyl derivatives of 1-chroman, that is 2,3-dihydro-1-benzopyran, to a process for their preparation and to pharmaceutical compositions containing them.

The invention provides compounds having the following general formula (I)

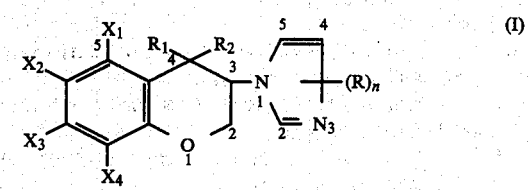

wherein
R is $C_1$-$C_6$ alkyl;
n is 0, 1, 2 or 3
one of $R_1$ and $R_2$ is hydroxy and the other is hydrogen or $C_1$-$C_6$ alkyl, or $R_1$ and $R_2$, taken together, form an oxo group;
each of $X_1$, $X_2$, $X_3$ and $X_4$, which may be the same or different, is hydrogen; halogen; hydroxy; $-NO_2$; $-CN$; $C_1$-$C_6$ alkyl; $C_1$-$C_6$ alkoxy; trihalo-$C_1$-$C_6$ alkyl; $-SR'$ or $-COOR'$, R' being hydrogen or $C_1$-$C_6$ alkyl;

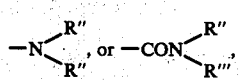

each of R" and R''', which may be the same or different, being hydrogen or $C_1$-$C_6$ alkyl; or one of $X_1$, $X_2$, $X_3$ and $X_4$ is phenyl, phenylthio, phenoxy or benzyl, the phenyl, phenylthio, phenoxy and benzyl groups being unsubstituted or substituted by halogen, $C_1$-$C_6$ alkyl, $C_{1-6}$ alkoxy, or $-SR'$, wherein R' is as defined above, and the others are as defined above; or any two adjacent $X_1$, $X_2$, $X_3$ and $X_4$ groups, taken together, complete a saturated or unsaturated 6-membered carbocyclic ring fused to the benzene ring shown in formula (I), the carbocyclic ring being unsubstituted or substituted by one or more groups selected from halogen, $C_1$-$C_6$ alkyl, $C_{1-6}$ haloalkyl, $C_1$-$C_6$ alkoxy or $-SR'$, wherein R' is as defined above, and any groups $X_1$ to $X_4$ not participating in the completion of such a fused ring are as defined above, and the pharmaceutically acceptable salts thereof.

The present invention includes all the possible isomers of formula (I) and their mixtures, as well as the metabolites and the metabolic precursors of the compounds of formula (I). The compounds of formula (I) in which one of $R_1$ and $R_2$ is hydroxy may be in the cis- or in the trans-configuration: both the single cis- and trans-isomers and their mixtures are included in the scope of the invention.

Pharmaceutically acceptable salts of the compounds of formula (I) include acid addition salts, with inorganic, e.g. nitric, hydrochloric, hydrobromic, sulphuric, perchloric and phosphoric, acids, or organic, e.g. acetic, propionic, glycolic, lactic, oxalic, malonic, malic, maleic, tartaric, citric, benzoic, cinnamic, mandelic and salicyclic acids, and salts with inorganic, e.g. alkali metal, especially sodium or potassium bases or alkaline-earth metal, especially calcium or magnesium bases, or with organic bases, e.g. alkylamines, preferably triethylamine.

The alkyl, alkoxy and alkylthio groups may be branched or straight chain groups.

A halogen atom is preferably fluorine, chlorine or bromine. A $C_1$-$C_6$ alkyl group is preferably isopropyl or tert.butyl. A $C_1$-$C_6$ alkoxy group is preferably methoxy or isopropoxy. A $C_1$-$C_6$ alkylthio group is preferably methylthio or isopropylthio.

A trihalo-$C_1$-$C_6$-alkyl is preferably trihalomethyl and more preferably trifluoromethyl.

Any two of $X_1$ to $X_4$ can complete a saturated or unsaturated fused ring. The adjacent participating $X_1$ to $X_4$ groups can be $X_2$ and $X_3$, $X_1$ and $X_2$, $X_3$ and $X_4$ or both $X_1$ and $X_2$ and $X_3$ and $X_4$. Each pair of participating $X_1$ to $X_4$ groups has the formula

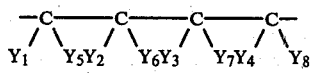

wherein each of the symbols $Y_1$ to $Y_8$, which may be the same or different represents hydrogen, halogen, $C_{1-6}$ alkyl, $C_{1-6}$ haloalkyl, especially trifluoromethyl, $C_{1-6}$ alkoxy or SR', R' being as defined above or $Y_5$ and $Y_6$ together and/or $Y_7$ and $Y_8$ together represent a carbon to carbon double bond and the remaining symbols $Y_1$ to $Y_8$ are as defined above. Preferably the pair of participating groups $X_1$ to $X_4$ complete a fused benzene ring unsubstituted or substituted as defined above, preferably by a halogen, preferably chlorine, atom.

Preferred compounds of the invention are the compounds of formula (I) wherein n is zero, one of $R_1$ and $R_2$ is hydrogen and the other is hydroxy, or $R_1$ and $R_2$, taken together, form an oxo group, and wherein $X_1$, $X_2$, $X_3$ and $X_4$ are, independently, hydrogen, halogen, hydroxy, carboxy, trifluoromethyl, $C_1$-$C_4$ alkylthio, $C_1$-$C_4$ alkyl, $C_1$-$C_4$ alkoxy, carbamoyl or

wherein R" and R''' are as defined above, or one of $X_1$, $X_2$, $X_3$ and $X_4$ is phenyl, phenylthio, phenoxy or benzyl, the phenyl, phenylthio, phenoxy and benzyl groups being unsubstituted or substituted by halogen, $C_1$-$C_4$ alkyl, $C_1$-$C_4$ alkylthio or $C_1$-$C_4$ alkoxy, and the others are independently, hydrogen, halogen, $C_1$-$C_4$ alkyl, $C_1$-$C_4$ alkylthio or $C_1$-$C_4$ alkoxy, as well as the pharmaceutically acceptable salts thereof.

Examples of preferred compounds of the invention are the following:
(1) 3-(1-imidazolyl)-2,3-dihydro-4H-1-benzopyran-4-one;
(2) 3-(1-imidazolyl)-2,3-dihydro-6-methyl-4H-1-benzopyran-4-one;
(3) 3-(1-imidazolyl)-2,3-dihydro-6-chloro-4H-1-benzopyran-4-one;
(4) 3-(1-imidazolyl)-2,3-dihydro-6-bromo-4H-1-benzopyran-4-one;
(5) 3-(1-imidazolyl)-2,3-dihydro-6-trifluoromethyl-4H-1-benzopyran-4-one;
(6) 3-(1-imidazolyl)-2,3-dihydro-6-methoxy-4H-1-benzopyran-4-one;

(7) 3-(1-imidazolyl)-2,3-dihydro-6-phenyl-4H-1-benzopyran-4-one;
(8) 3-(1-imidazolyl)-2,3-dihydro-6-phenoxy-4H-1-benzopyran-4-one;
(9) 3-(1-imidazolyl)-2,3-dihydro-7-chloro-4H-1-benzopyran-4-one;
(10) 3-(1-imidazolyl)-2,3-dihydro-7-phenyl-4H-1-benzopyran-4-one;
(11) 3-(1-imidazolyl)-2,3-dihydro-6,8-dichloro-4H-1-benzopyran-4-one;
(12) 3-(1-imidazolyl)-2,3-dihydro-6,8-dibromo-4H-1-benzopyran-4-one;
(13) 3-(1-imidazolyl)-2,3-dihydro-5,7-dichloro-4H-1-benzopyran-4-one;
(14) 3-(1-imidazolyl)-2,3-dihydro-7-methoxy-4H-1-benzopyran-4-one.
(15) 3-(1-imidazolyl)-2,3-dihydro-6-hydroxy-8-n-propyl-4H-1-benzopyran-4-one.
(16) 3-(1-imidazolyl)-2,3-dihydro-7-isopropyloxy-4H-1-benzopyran-4-one.
(17) 3-(1-imidazolyl)-2,3-dihydro-5,7-diisopropyl-6-hydroxy-4H-1-benzopyran-4-one.
(18) 3-(1-imidazolyl)-2,3-dihydro-7-hydroxy-4H-1-benzopyran-4-one.
(19) 3-(1-imidazolyl)-2,3-dihydro-6-bromo-7-hydroxy-4H-1-benzopyran-4-one.
(20) 3-(1-imidazolyl)-2,3-dihydro-6,8-dibromo-7-hydroxy-4H-1-benzopyran-4-one.
(21) 3-(1-imidazolyl)-2,3-dihydro-6-chloro-7-hydroxy-4H-1-benzopyran-4-one.
(22) 3-(1-imidazolyl)-2,3-dihydro-6-tert.butyl-7-hydroxy-4H-1-benzopyran-4-one.
(23) 3-(1-imidazolyl)-2,3-dihydro-6-isopropyl-7-hydroxy-4H-1-benzopyran-4-one.
(24) 3-(1-imidazolyl)-2,3-dihydro-6-tert.butyl-7-hydroxy-8-isopropyl-4H-1-benzopyran-4-one.
(25) 3-(1-imidazolyl)-2,3-dihydro-6,8-diisopropyl-7-hydroxy-4H-1-benzopyran-4-one.
(26) 3-(1-imidazolyl)-2,3-dihydro-7-bromo-4H-1-benzopyran-4-one.
(27) 3-(1-imidazolyl)-2,3-dihydro-5,7-dibromo-6-hydroxy-4H-1-benzopyran-4-one.
(28) 3-(1-imidazolyl)-2,3-dihydro-6-hydroxy-4H-1-benzopyran-4-one.
(29) 3-(1-imidazolyl)-2,3-dihydro-6-hydroxy-8-bromo-4H-1-benzopyran-4-one.
(30) 3-(1-imidazolyl)-2,3-dihydro-6-hydroxy-8-chloro-4H-1-benzopyran-4-one.
(31) 3-(1-imidazolyl)-2,3-dihydro-6-hydroxy-8-isopropyl-4H-1-benzopyran-4-one.
(32) 3-(1-imidazolyl)-2,3-dihydro-5,8-dibromo-6-hydroxy-4H-1-benzopyran-4-one.
(33) 3-(1-imidazolyl)-2,3-dihydro-5,7-ditert.butyl-6-hydroxy-4H-1-benzopyran-4-one.
(34) 3-(1-imidazolyl)-2,3-dihydro-5-hydroxy-6-tert.butyl-4H-1-benzopyran-4-one.
(35) 3-(1-imidazolyl)-2,3-dihydro-5-hydroxy-6-tert.butyl-8-isopropyl-4H-1-benzopyran-4-one.
(36) 3-(1-imidazolyl)-2,3-dihydro-6-methyl-8-bromo-4H-1-benzopyran-4-one.
(37) 3-(1-imidazolyl)-2,3-dihydro-6-tert.butyl-7-hydroxy-8-bromo-4H-1-benzopyran-4-one.
(38) 3-(1-imidazolyl)-2,3-dihydro-6-amino-8-bromo-4H-1-benzopyran-4-one.
(39) 3-(1-imidazolyl)-2,3-dihydro-6-dimethylamino-8-bromo-4H-1-benzopyran-4-one.
(40) 3-(1-imidazolyl)-2,3-dihydro-6-tert.butyl-4H-1-benzopyran-4-one.
(41) 3-(1-imidazolyl)-2,3-dihydro-6-carbamoyl-4H-1-benzopyran-4-one.
(42) 3-(1-imidazolyl)-2,3-dihydro-6-carboxy-4H-1-benzopyran-4-one.
(43) 3-(1-imidazolyl)-2,3-dihydro-6-carbamoyl-8-bromo-4H-1-benzopyran-4-one.
(44) 3-(1-imidazolyl)-2,3-dihydro-6-carboxy-8-bromo-4H-1-benzopyran-4-one.
(45) 3-(1-imidazolyl)-2,3-dihydro-6-carboxy-8-n-propyl-4H-1-benzopyran-4-one.
(46) 3-(1-imidazolyl)-2,3-dihydro-6-carbamoyl-8-n-propyl-4H-1-benzopyran-4-one.
(47) 3-(1-imidazolyl)-2,3-dihydro-7-tert.butyl-4H-1-benzopyran-4-one.
(48) 3-(1-imidazolyl)-2,3-dihydro-6,8-ditert.butyl-4H-1-benzopyran-4-one.
(49) 3-(1-imidazolyl)-2,3-dihydro-6-hydroxy-7-tert.butyl-4H-1-benzopyran-4-one.
(50) 3-(1-imidazolyl)-2,3-dihydro-6-tert.butyl-8-bromo-4H-1-benzopyran-4-one.
(51) 3-(1-imidazolyl)-2,3-dihydro-4H-1-benzopyran-4-ol;
(52) 3-(1-imidazolyl)-2,3-dihydro-6-chloro-4H-1-benzopyran-4-ol;
(53) 3-(1-imidazolyl)-2,3-dihydro-6-bromo-4H-1-benzopyran-4-ol;
(54) 3-(1-imidazolyl)-2,3-dihydro-6-methoxy-4H-1-benzopyran-4-ol;
(55) 3-(1-imidazolyl)-2,3-dihydro-6-phenyl-4H-1-benzopyran-4-ol;
(56) 3-(1-imidazolyl)-2,3-dihydro-7-chloro-4H-1-benzopyran-4-ol;
(57) 3-(1-imidazolyl)-2,3-dihydro-6,8-dichloro-4H-1-benzopyran-4-ol;
(58) 3-(1-imidazolyl)-2,3-dihydro-6,8-dibromo-4H-1-benzopyran-4-ol;
(59) 3-(1-imidazolyl)-2,3-dihydro-6-tert.butyl-7-hydroxy-4H-1-benzopyran-4-ol.
(60) 3-(1-imidazolyl)-2,3-dihydro-6-bromo-7-hydroxy-4H-1-benzopyran-4-ol.
(61) 3-(1-imidazolyl)-2,3-dihydro-6-tert.butyl-4H-1-benzopyran-4-ol.
(62) 3-(1-imidazolyl)-2,3-dihydro-6,8-dibromo-7-hydroxy-4H-1-benzopyran-4-ol.
(63) 3-(1-imidazolyl)-2,3-dihydro-6-hydroxy-8-bromo-4H-1-benzopyran-4-ol.
(64) 3-(1-imidazolyl)-2,3-dihydro-7-methoxy-4H-1-benzopyran-4-ol.

as well as the pharmaceutically acceptable salts thereof. The 4-ols can be in the form of cis or trans isomers or mixtures thereof.

The structural formulae of the above-numbered compounds, indicated according to their progressive number, are reported in the following Table.

TABLE

| COMPOUND | $X_1$ | $X_2$ | $X_3$ | $X_4$ | $R_1$ | $R_2$ |
|---|---|---|---|---|---|---|
| 1 | H | H | H | H | | =O |
| 2 | H | $CH_3$ | H | H | | =O |
| 3 | H | Cl | H | H | | =O |

TABLE -continued

| COMPOUND | $X_1$ | $X_2$ | $X_3$ | $X_4$ | $R_1$ | $R_2$ |
|---|---|---|---|---|---|---|
| 4 | H | Br | H | H | | $=O$ |
| 5 | H | $CF_3$ | H | H | | $=O$ |
| 6 | H | $OCH_3$ | H | H | | $=O$ |
| 7 | H | $C_6H_5$ | H | H | | $=O$ |
| 8 | H | $C_6H_5O$ | H | H | | $=O$ |
| 9 | H | H | Cl | H | | $=O$ |
| 10 | H | H | $C_6H_5$ | H | | $=O$ |
| 11 | H | Cl | H | Cl | | $=O$ |
| 12 | H | Br | H | Br | | $=O$ |
| 13 | Cl | H | Cl | H | | $=O$ |
| 14 | H | H | $CH_3O$ | H | | $=O$ |
| 15 | H | OH | H | n-Pr | | $=O$ |
| 16 | H | H | $(CH_3)_2CHO$ | H | | $=O$ |
| 17 | i-Pr | OH | i-Pr | H | | $=O$ |
| 18 | H | H | OH | H | | $=O$ |
| 19 | H | Br | OH | H | | $=O$ |
| 20 | H | Br | OH | Br | | $=O$ |
| 21 | H | Cl | OH | H | | $=O$ |
| 22 | H | tert-Bu | OH | H | | $=O$ |
| 23 | H | i-Pr | OH | H | | $=O$ |
| 24 | H | tert-Bu | OH | i-Pr | | $=O$ |
| 25 | H | i-Pr | OH | i-Pr | | $=O$ |
| 26 | H | H | Br | H | | $=O$ |
| 27 | Br | OH | Br | H | | $=O$ |
| 28 | H | OH | H | H | | $=O$ |
| 29 | H | OH | H | Br | | $=O$ |
| 30 | H | OH | H | Cl | | $=O$ |
| 31 | H | OH | H | i-Pr | | $=O$ |
| 32 | Br | OH | H | Br | | $=O$ |
| 33 | tert-Bu | OH | tert-Bu | H | | $=O$ |
| 34 | OH | tert-Bu | H | H | | $=O$ |
| 35 | OH | tert-Bu | H | i-Pr | | $=O$ |
| 36 | H | $CH_3$ | H | Br | | $=O$ |
| 37 | H | tert-Bu | OH | Br | | $=O$ |
| 38 | H | $NH_2$ | H | Br | | $=O$ |
| 39 | H | $(CH_3)_2N-$ | H | Br | | $=O$ |
| 40 | H | tert-Bu | H | H | | $=O$ |
| 41 | H | $CONH_2$ | H | H | | $=O$ |
| 42 | H | COOH | H | H | | $=O$ |
| 43 | H | $CONH_2$ | H | Br | | $=O$ |
| 44 | H | COOH | H | Br | | $=O$ |
| 45 | H | COOH | H | n-Pr | | $=O$ |
| 46 | H | $CONH_2$ | H | n-Pr | | $=O$ |
| 47 | H | H | tert-Bu | H | | $=O$ |
| 48 | H | tert-Bu | H | tert-Bu | | $=O$ |
| 49 | H | OH | tert-Bu | H | | $=O$ |
| 50 | H | tert-Bu | H | Br | | $=O$ |
| 51 | H | H | H | H | H | OH |
| 52 | H | Cl | H | H | H | OH |
| 53 | H | Br | H | H | H | OH |
| 54 | H | $OCH_3$ | H | H | H | OH |
| 55 | H | $C_6H_5$ | H | H | H | OH |
| 56 | H | H | Cl | H | H | OH |
| 57 | H | Cl | H | Cl | H | OH |
| 58 | H | Br | H | Br | H | OH |
| 59 | H | tert-Bu | OH | H | H | OH |
| 60 | H | Br | OH | H | H | OH |
| 61 | H | tert-Bu | H | H | H | OH |
| 62 | H | Br | OH | Br | H | OH |
| 63 | H | OH | H | Br | H | OH |
| 64 | H | H | $OCH_3$ | H | H | OH |

In the above table the abbreviations i-Pr and tert-Bu mean isopropyl and tert.butyl respectively. In all the above listed compounds n represents zero.

The compounds of formula (I) in which $R_1$ and $R_2$ together represent an oxo group can be prepared by a process comprising:

(a) reacting a compound of formula (II)

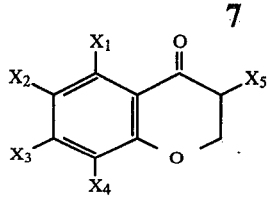

wherein $X_1$, $X_2$, $X_3$ and $X_4$ are as defined above and $X_5$ is halogen or a reactive ester group, with a compound of formula (III)

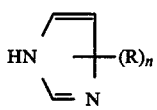

wherein

R and n are as defined above or a salt thereof, thus giving a compound of formula (I) wherein $R_1$ and $R_2$, taken together, form an oxo group and R, n, $X_1$, $X_2$, $X_3$ and $X_4$ are as defined above, or (b) reacting a compound of formula (IV)

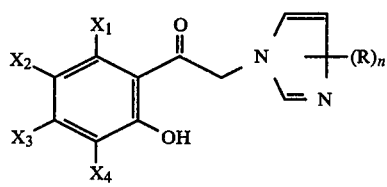

wherein $X_1$, $X_2$, $X_3$, $X_4$, R and n are as defined above, with formaldehyde or a reactive derivative thereof, thus giving a compound of formula (I) wherein $R_1$ and $R_2$, taken together, form an oxo group and R, n, $X_1$, $X_2$, $X_3$ and $X_4$ are as defined above.

The compounds of formula (I) in which one of $R_1$ and $R_2$ is hydroxy and the other hydrogen can be prepared by reducing a compound of formula (V), i.e. a compound of formula (I) in which $R_1$ and $R_2$ together represent an oxo group,

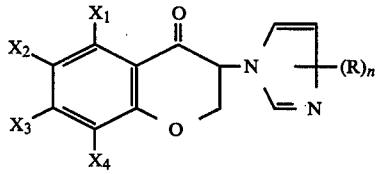

wherein

R, n, $X_1$, $X_2$, $X_3$ and $X_4$ are as defined above, thus giving a compound of formula (I) wherein one of $R_1$ and $R_2$ is hydrogen and the other is hydroxy and R, n, $X_1$, $X_2$, $X_3$ and $X_4$ are as defined above.

The compounds of the invention of formula (I) in which one of $R_1$ and $R_2$ is hydroxy and the other $C_{1-6}$ alkyl can be prepared by reacting a compound of formula (V) wherein R, n, $X_1$, $X_2$, $X_3$ and $X_4$ are as defined above with a compound of formula (VI)

$R_3\text{-}Z$ (VI)

wherein

Z is Li or the group MgX, in which X is halogen, and $R_3$ is $C_1$-$C_6$ alkyl, thus giving a compound of formula (I) wherein one of $R_1$ and $R_2$ is hydroxy and the other is $C_1$-$C_6$ alkyl and R, n, $X_1$, $X_2$, $X_3$ and $X_4$ are as defined above.

Further, if desired, any of the above processes can include a step of converting a compound of formula (I) into another compound of formula (I), and/or removing a protective group, and/or, if desired, converting a compound of formula (I) into a pharmaceutically acceptable salt thereof and/or, if desired, converting a salt into a free compound and/or, if desired, separating a mixture of isomers of formula (I) into the single isomers.

When in the compound of formula (II) $X_5$ is a halogen atom, it is preferably chlorine or bromine and when it is a reactive ester group, it is preferably —O-tosyl or —O-mesyl. A salt of a compound of formula (III) is preferably an alkali metal e.g. sodium or potassium salt or a silver salt. The reaction of a compound of formula (II) with a compound of formula (III) or a salt thereof is preferably carried out either (a) in the absence of solvent, at a temperature preferably ranging between the room temperature and 180° C. and for reaction times which may vary from some minutes to about 20 hours using, if necessary, an excess of the compound of formula (III) or a salt thereof, or (b) in the presence of a suitable solvent, preferably dimethylformamide, dimethylacetamide, hexamethylphosphorotriamide, benzene, toluene, ethyl acetate, ethyl alcohol, dioxane or acetone, at a temperature preferably ranging between about 0° C. and the reflux temperature, for reaction times varying from some minutes to about 12 hours and using, if necessary, an excess of the compound with formula (III) or a stoichiometric amount of a tertiary base, preferably triethylamine. The reaction of a compound of formula (IV) with formaldehyde or a reactive derivative thereof, which may be, for instance, trioxymethylene, may be performed by using aqueous or aqueous-lcoholic solutions of formaldehyde, paraformaldehyde, or trioxymethylene, in a suitable solvent, e.g. methyl or ethyl alcohol or acetic acid, at a temperature preferably ranging between about the room temperature and the reflux temperature for reaction times varying from few minutes to some hours.

The reduction of a compound of formula (V) may be, for example, performed (a) by treatment with an alkali metal boronhydride, e.g. $NaBH_4$, in a suitable solvent, e.g. methyl or ethyl alcohol or a mixture of water and ethyl alcohol, or (b) by treatment with $LiAlH_4$ in an anhydrous solvent, e.g. diethyl ether or tetrahydrofuran, at a temperature ranging, in both cases, preferably between 0° C. and the reflux temperature, for reaction times varying approximately from 1 to 6 hours.

Alternatively the reduction of a compound of formula (V) may be carried out by catalytic hydrogenation in the presence of a suitable catalyst, e.g. palladium, platinum, $PtO_2$, ruthenium or Raney-nickel in a suitable solvent, preferably chosen from methyl alcohol, ethyl alcohol, acetic acid, cyclohexane, n-hexane, ethyl acetate, benzene or toluene and operating at a pressure ranging from atmospheric pressure to about 50 atmospheres and at a temperature ranging from about 20° C. to about 100° C.

When in the compounds of formula (V) one or more of $X_1$, $X_2$, $X_3$ and $X_4$ are reducible groups, e.g. —$NO_2$, —CN, —COOR' or

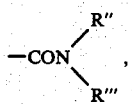

the reduction is preferably performed with an alkali metal boronhydride, preferably NaBH$_4$, in order to avoid the simultaneous reduction of such reducible groups. When in the compound of formula (VI) Z is —MgX, in the Grignard reagent of formula R$_3$MgX, X is preferably iodine or bromine.

The reaction of a compound of formula (V) with a compound of formula R$_3$MgX may be performed in an anhydrous suitable solvent, preferably an ether, conveniently anhydrous diethyl ether, and at temperatures ranging from about 0° C. to the room temperature.

The reaction of a compound of formula (V) with a compound of formula (VI) wherein Z is Li, that is a lithium-alkyl of formula LiR$_3$, wherein R$_3$ is as defined above, may be carried out, for example, in a suitable anhydrous solvent, which may be, for instance, n-hexane or n-pentane, at a temperature ranging from about −60° C. to about −80° C., preferably at approximately −78° C.

A compound of formula (I) may be converted, if desired, into another compound of formula (I).

These optional conversions may be carried out by methods known in themselves.

Thus, for example, a compound of formula (I) wherein one or more of X$_1$, X$_2$, X$_3$ and X$_4$ is hydrogen may be converted into a compound of formula (I) wherein one or more of X$_1$, X$_2$, X$_3$ and X$_4$ is a halogen atom, e.g. chlorine or bromine, by reaction with chlorine or bromine in the presence of a Friedel-Crafts catalyst, preferably AlCl$_3$, operating in a suitable solvent, e.g. CH$_2$Cl$_2$.

A compound of formula (I) wherein one or more of X$_1$, X$_2$, X$_3$ and X$_4$ is an esterified carboxy group may be converted into a compound of formula (I) wherein one or more of X$_1$, X$_2$, X$_3$ and X$_4$ is a free carboxy group, by hydrolysis in a solvent, such as water or a lower aliphatic alcohol, operating at a temperature ranging from the room temperature to about 150° C.; the same reaction may be also performed by treatment with lithium bromide in dimethylformamide, at a temperature higher than 50° C.

A compound of formula (I), wherein one or more of X$_1$, X$_2$, X$_3$ and X$_4$ is —CONH$_2$, may be converted into a compound of formula (I), where one or more of X$_1$, X$_2$, X$_3$ and X$_4$ is a free carboxy group, by hydrolysis, preferably by acid hydrolysis, in a suitable solvent, such as water, or by the Bouveault procedure, that is by treatment with NaNO$_2$ and an aqueous strong inorganic acid, i.e. H$_2$SO$_4$, operating at temperatures ranging from the room temperature and 100° C.

A compound of formula (I) wherein one or more of X$_1$, X$_2$, X$_3$ and X$_4$ is a free carboxy group may be converted into a compound of formula (I) wherein one or more of X$_1$, X$_2$, X$_3$ and X$_4$ is an esterified carboxy group, i.e. an alkoxycarbonyl group, by reaction, for example, of the alkali metal salt of the acid with a suitable alkyl halide, in an inert solvent, such as acetone, dioxane, dimethylformamide, hexamethylphosphorotriamide, at a temperature ranging from about 0° C. to about 100°.

A compound of formula (I), wherein one or more X$_1$, X$_2$, X$_3$ and X$_4$ is hydrogen may be converted into a compound of formula (I), where one or more of X$_1$, X$_2$, X$_3$ and X$_4$ is C$_1$–C$_6$ alkyl, by alkylation through a Friedel-Crafts reaction, followed by reaction with a C$_1$–C$_6$ alkylhalide, preferably chloride, bromide or iodide, or with a C$_1$–C$_6$ alcohol in a suitable solvent, e.g. nitrobenzene or CH$_2$Cl$_2$, or CS$_2$, the latter in the presence of appropriate amount of a Friedel-Crafts catalyst, such as AlCl$_3$, ZnCl$_2$ or BF$_3$, the latter in the presence of a strong mineral acid as HF, HClO$_4$ or, if desired, in concentrated H$_2$SO$_4$ or in concentrated H$_3$PO$_4$ without additional solvent, at temperatures ranging from the room temperature to 100° C.

A compound of formula (I) wherein one or more of X$_1$, X$_2$, X$_3$ and X$_4$ is a C$_1$–C$_6$ alkoxy group may be converted into a compound of formula (I) wherein one or more of X$_1$, X$_2$, X$_3$ and X$_4$ is a hydroxy group by following conventional procedures well known in organic chemistry. For example by treatment with a strong mineral acid, i.e. HCl, HBr, HI, preferably HBr, at temperature ranging from 30° C. to the reflux temperature, preferably at reflux temperature, or by treatment with a Lewis acid, for example AlCl$_3$ or BF$_3$, in a suitable solvent i.e. CH$_2$Cl$_2$ or nitrobenzene, at temperature ranging from the room temperature to 80° C.

Also the optional salification of a compound of formula (I) as well as the conversion of a salt into the free compound and the separation of a mixture of isomers into the single isomers may be carried out by conventional methods.

For example the separation of a mixture of geometric isomers, e.g. cis- and trans-isomers, may be carried out by fractional crystallization from a suitable solvent or by chromatography; either column chromatography or high pressure liquid chromatography.

A compound of formula (II) in which X$_5$ is a halogen atom may be obtained halogenating the corresponding compound of formula (VII)

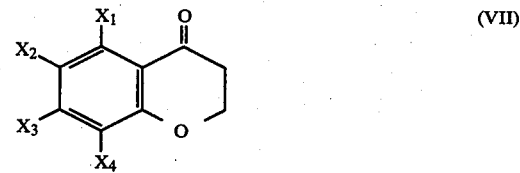

wherein

X$_1$, X$_2$, X$_3$ and X$_4$ are as defined above. The halogenation of a compound of formula (VII) to give a compound of formula (II) is usually carried out with a stoichiometric amount of halogen, preferably bromine or chlorine, in a suitable solvent, e.g. diethyl ether, methylene chloride, CHCl$_3$, CCl$_4$, CS$_2$ or acetic acid, at a temperature ranging from about 0° C. to about 100° C., for reaction times ranging approximately between 3 and 12 hours. Alternatively, the halogenation reaction of a compound of formula (VII) may be carried out by using a stoichiometric amount of sulphuryl chloride in a suitable solvent, e.g. methylene chloride, chloroform or benzene at temperatures ranging from the room to the reflux temperature, for reaction times ranging from 3 to 12 hours.

A compound of formula (II) wherein X$_5$ is -O-tosyl or -O-mesyl may be obtained by reacting the corresponding alcohol, that is a compound of formula (II) wherein X$_5$ is hydroxy [which is known or may be prepared by known methods], with p-toluenesulphonyl or methanesulphonyl halide, preferably the chloride.

The reaction is preferably carried out in an anhydrous inert solvent, e.g. acetone, at temperatures ranging from the room to the reflux temperature.

The compounds of formula (III) are known or may be obtained by known methods starting from known compounds.

A compound of formula (IV) may be obtained by reacting a compound of formula (VIII)

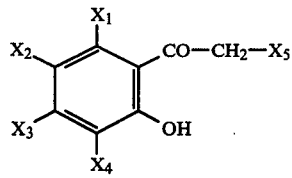

(VIII)

wherein $X_1$, $X_2$, $X_3$, $X_4$ and $X_5$ are as defined above, with a compound of formula (III) or a salt thereof, preferably an alkali metal, e.g. sodium or potassium salt or a silver salt. The reaction may be carried out using the same reaction conditions reported above for the reaction between a compound of formula (II) and a compound of formula (III).

The compound of formula (V) is a compound of formula (I) wherein $R_1$ and $R_2$, taken together, form an oxo group and may be obtained by the process (a) or (b) described above.

The compounds of formula (VI) are known compounds. Also the compounds of formula (VII) are known or they may be prepared by known methods from known compounds. For instance, a compound of formula (VII) in which $X_1$, $X_2$, $X_3$ and $X_4$ are as defined above, may be obtained by cyclizing a compound of formula (IX)

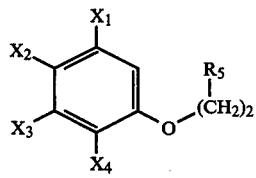

(IX)

wherein $R_5$ is cyano, carboxy, ($C_1$-$C_7$ alkoxy)carbonyl or the group —$COX_6$, wherein $X_6$ is a halogen atom and $X_1$, $X_2$, $X_3$ and $X_4$ are as defined above.

The cyclization of a compound of formula (IX) in which $R_5$ is cyano, carboxy or ($C_1$-$C_7$ alkoxy)carbonyl, may be carried out by treatment with a suitable cyclizing agent, e.g. phosphoric anhydride, polyphosphoric acid, chlorosulphonic acid or sulphuric acid, optionally in the presence of a suitable solvent, preferably chosen from benzene, toluene and xylene, at a temperature which may range from about 20° C. to about 130° C. The cyclisation of a compound with formula (IX) wherein $R_5$ is the group —$COX_6$ and $X_6$ is as defined above, is preferably carried out by using $AlCl_3$ in the presence of a suitable solvent, e.g. carbon disulfide, methylene chloride or carbon tetrachloride, at temperatures ranging from about 0° C. to about 50° C.

The compounds of formula (VIII) and (IX) are known or may be prepared by known methods, starting from known compounds. For example, a compound of formula (IX) in which $X_1$, $X_2$, $X_3$ and $X_4$ are as defined above and $R_5$ is cyano, carboxy on ($C_1$-$C_7$ alkoxy)carbonyl may be obtained by reacting a compound of formula (X)

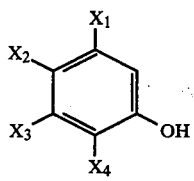

(X)

wherein $X_1$, $X_2$, $X_3$ and $X_4$ are as defined above, or a reactive derivative thereof, with a compound of formula (XI)

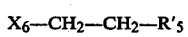

$X_6$—$CH_2$—$CH_2$—$R'_5$ (XI)

wherein $X_6$ is halogen, preferably chlorine or bromine, and $R'_5$ is cyano, carboxy, or ($C_1$-$C_7$ alkoxy)carbonyl.

Alternatively, a compound of formula (IX) wherein $R_5$ is a carboxy group, may be obtained by reacting a compound of formula (X), or a reactive thereof, with β-propionolactone; a compound of formula (IX) in which $R_5$ is cyano, may be obtained by reacting a compound of formula (X) or a reactive thereof, with acrylonitrile; a compound of formula (IX) in which $R_5$ is ($C_1$-$C_7$ alkoxy)carbonyl, may be obtained by reacting a compound of formula (X), or a reactive thereof, with the appropriate alkyl acrylate. A reactive derivative of a compound with formula (X) may be, for example, a salt, e.g. an alkali metal (sodium or potassium, for instance,) salt. The compounds of formula (X) as well as the reactive derivatives thereof, are known compounds or may be obtained by known methods starting from known compounds. The reaction of a compound of formula (X) with a compound of formula (XI) or with β-propionolactone, is preferably carried out by using a salt of the compound of formula (X), preferably an alkali metal e.g. sodium salt, in a suitable solvent, e.g. water or a mixture of water and ethyl alcohol, preferably at the reflux temperature.

The reaction of a compound of formula (X) with acrylonitrile or an alkyl acrylate is preferably carried out in the absence of solvents but in the presence of "Triton B" and at the reflux temperature. "Triton" is a trade mark.

The compounds of formula (X) and (XI) are known or may be obtained by known methods.

When in the compounds having the formulae (I), (II), (IV), (V), (VII), (VIII), (IX) and (X) groups are present which need to be protected during the reactions reported above, e.g. amino, hydroxy, further carboxy groups, etc., such groups can be protected in a conventional way before the reaction takes place.

Examples of protecting groups are those usually employed in the synthesis of peptides, for example, to protect amino groups, acetyl, benzoyl, tert.butoxy-carbonyl, p-methoxy-benzyloxy-carbonyl, o-nitro-phenylsulphonyl, dichloroacetyl or tert.butyl-dimethylsilyl protective groups may be employed. To protect hydroxy groups (a useful step e.g. when converting a compound of formula (VIII) into a compound of formula (IV) as reported above) acetyl, benzoyl or benzyloxy groups may be, for instance, employed. To protect the carboxy group, tert.butyl, benzhydryl and p-methoxy-benzyl groups may be employed. The protecting groups are then removed, at the end of the reaction, in a known manner, e.g. by mild acid hydrolysis or by mild catalytic reduction, for example with Pd/C as catalyst at atmospheric pressure.

The compounds of the present invention possess an elevated lipid lowering and antiatherosclerotic activity. In particular the compounds of the invention are active in lowering cholesterol and triglycerides, in increasing the total serum HDL cholesterol, as well as in increasing the ratio between α-lipoprotein and β-lipoprotein total cholesterol. [As is known, drugs selectively increasing the HDL-cholesterol concentration in blood and/or the ratio between α and β lipoprotein cholesterol are useful in prevention and therapy of atherosclerosis: Glueck C. J., Artery, 2, 196 (1976); Day C. E. in Frank-H-Clarke (Ed.) Annual Reports in Medicinal Chemistry, 13, 184, Chapter 20-Academic Press, N.Y. 1978].

The activity of the compounds of the invention was evaluated on groups of Icem: CER (SPF Caw) male rats either fed for six days with hypercholesterolaemic diet according to C. E. Day [Schurr P. E., Schultz H. R., Day C. E. (Eds) Atherosclerosis and drug discovery—Plenum Pub. Corp., 217 (1976)] (Experiment No. 1) or fed standard diet Altromin (Experiment No. 2). "Altromin" is a trade mark.

The compounds were suspended in "Methocel" (methyl cellulose, a 0.5% suspension in water) and administered by stomach tube at the dose of 50 mg/kg for 4 days.

Groups of animals were treated with the suspending agent only (control groups).

The total serum cholesterol was determined with the method of Trinder P. J. [J. Clin. Pathol., 22, 246 (1969)].

The serum triglycerides were determined with the method of Mendez J. [J. Clin. Chem., 21, 768, (1975)].

The total serum HDL cholesterol was determined according to Demacker P. N. M. [Clin. Chem., 23, 1238, (1977)]. The total β-lipoprotein cholesterol was determined by difference between total serum cholesterol and HDL cholesterol.

Statistical analysis in experiment No. 1 was performed by the Student's test for independent samples or by the Cochran's t test when the variances were not homogeneous at the F ratio test [Bliss C. I.—Statistics in Biology, Vol. 1, page 213—Mc Graw Hill Book Company, New York, 1967; Cochran W. G., Cox G. M.—Experimental designs—J. Wiley e Sons Inc., New York, II Ed. (1968) page 100].

For the experiment No. 2 the following statistical methods were applied: the variance analysis, Bartlett test [Properties of sufficiency and Statistical Tests—Proc. of the Royal Soc. of London A 160 (1937) pages 268–282] to prove the variance homogeneity and the Dunnett test [Dunnett C. W.—J. Amer. Stat. Ass., 50, 1096 (1955)]. Taking in account the ratio between α and β lipoprotein cholesterol it was necessary to make the variances homogeneous by a transformation of the values ($\sqrt{x}$).

In the animals treated with hypercholesterolaemic diet the tested compounds were found to decrease the total serum cholesterol, to increase the total serum HDL cholesterol and the ratio between α and β lipoprotein total cholesterol. The Table 1 reports the values of serum total cholesterol and total HDL cholesterol and ratio between α and β lipoprotein total cholesterol from animals fed hypercholesterolaemic diet and treated with two compounds of the invention: 3-(1-imidazolyl)-2,3-dihydro-6-chloro-4H-1-benzopyran-4-one: compound A, and 3-(1-imidazolyl)-2,3-dihydro-6-chloro-4H-1-benzopyran-4-ol (trans isomer): compound B, in comparison with the values of the same variables in controls.

TABLE 1

(Experiment No 1)

| Treatment | Dose mg/kg/os | Animals number | Total serum cholesterol mg/100 ml mean ± S.E. | Result | Serum HDL total cholesterol mg/100 ml mean ± S.E. | Result | α/β lipoprotein cholesterol mean ± S.E. | Result |
|---|---|---|---|---|---|---|---|---|
| Control | * | 10 | 386.1 ± 39.6 | | 17.8 ± 1.1 | | 0.0597 ± 0.010 | |
| Compound A | 50 | 10 | 133.2 ± 10.1 | *** | 44.3 ± 1.3 | *** | 0.548 ± 0.052 | *** |
| Control | * | 5 | 447.8 ± 14.3 | | 19.0 ± 0.8 | | 0.0444 ± 0.002 | |
| Compound B | 50 | 5 | 184.4 ± 19.7 | *** | 47.6 ± 2.4 | *** | 0.3664 ± 0.055 | *** |

*"Methocel" (0.5% in distilled water): 5 ml/kg/os
***HS = highly significant ($p < 0.01$)

In the animals fed standard "Altromin" diet the tested compounds were found to decrease both the total serum cholesterol and the serum triglycerides and also to increase both the HDL cholesterol and the ratio between α and β lipoprotein total cholesterol.

The Table 2 shows the values of total serum cholesterol, triglycerides, HDL cholesterol and of the ratio α and β lipoprotein total cholesterol in animals fed standard diet and treated with the same compounds cited in Table 1, in comparison with the values in control animals.

TABLE 2

(Experiment No. 2)

| Treatment | Dose mg/kg/os | Animals number | Total serum cholesterol mg/100 ml mean ± S.E. | Result | Serum triglycerides mg/100 ml mean ± S.E. | Result | Serum HDL total cholesterol mg/100 ml mean ± S.E. | Result | α/β lipoprotein total cholesterol mean ± S.E. | Result |
|---|---|---|---|---|---|---|---|---|---|---|
| Control | * | 10 | 88.9 ± 2.3 | | 142.0 ± 6.2 | | 43.5 ± 1.4 | | 0.983 ± 0.018 | |
| Compound A | 50 | 10 | 73.4 ± 3.0 | *** | 77.2 ± 7.0 | *** | 52.3 ± 2.5 | ** | 1.450 ± 0.054 | *** |
| Compound B | 50 | 10 | 72.4 ± 2.3 | *** | 90.6 ± 6.1 | *** | 50.3 ± 1.7 | ** | 1.432 ± 0.046 | *** |

*"Methocel" 0.5% in distilled water, 5 ml/kg/os
**S = significant ($p < 0.05$)
***HS = highly significant ($p < 0.01$)

The compounds of the invention are also endowed with blood platelet-antiaggregating activity. This activity was evaluated e.g. "in vitro" on the basis of the ability of the test compounds to inhibit the collagen-induced platelet aggregation in Guinea pig platelet rich plasma according to the method of Born "Born G.V.R.—Nature, 1942, 927 (1962)]. The compounds of the invention were found to have a strong platelet aggregation inhibiting activity: for example, the compound 3-(1-imidazolyl)-2,3-dihydro-6-chloro-4H-1-benzopyran-4-one was found to inhibit wholly, at the final 25 mcg/ml concentration, the platelet aggregation induced by a 2 mcg/ml concentration of collagen.

In view of their elevated lipid lowering activity, of their action on HDL cholesterol and in view of their platelet antiaggregating activity, the compounds of the invention, in particular: 3-(1-imidazolyl)-2,3-dihydro-6-chloro-4H-1-benzopyran-4-one; 3-(1-imidazolyl)-2,3-dihydro-6-tert.butyl-7-hydroxy-4H-1-benzopyran-4-one and 3-(1-imidazolyl)-2,3-dihydro-6,8-dibromo-4H-1-benzopyran-4-one, are useful in the treatment of dislipidaemies and of the atherosclerotic syndrome as well as in the prevention and treatment of syndromes caused by platelet aggregation disorders such as, for example, thrombosis.

The toxicity of the compounds of the invention was found to be quite negligible and therefore they can be safely used in therapy. The evaluation of the toxicity (as orientative acute toxicity, i.e. $LD_{50}$), was carried out, e.g., as follows: nine hours food deprived mice were treated orally with single administration of increasing doses, then housed and normally fed; the $LD_{50}$ was assessed on the seventh day after the treatment.

For example, the $LD_{50}$ of the compounds of the above Tables was about 800 mg/kg. Similar $LD_{50}$ values have been found for the other compounds of the invention. The compounds of the invention can be administered in a variety of dosage forms, e.g. orally, in the form of tablets, capsules, sugar or film coated tablets, liquid solution or suspensions, rectally, in the form of suppositories, parenterally, e.g. intramuscularly, or by intravenous injection or infusion.

The dosage depends on the age, weight, conditions of the patient and administration route; for example the dosage adopted for oral administration to adult humans ranges from about 50 to about 200 mg pro dose, from 1 to 3 times daily, preferably from 50 to 100 mg pro dose 1-3 times a day. The invention includes pharmaceutical compositions comprising a compound of the invention in association with a pharmaceutically acceptable excipient (which can be a carrier or diluent).

The pharmaceutical compositions containing the compounds of the invention are usually prepared following conventional methods and are administered in a pharmaceutically suitable form.

For example, the solid oral forms may contain, together with the active compound, diluents, e.g., lactose, dextrose, saccharose, cellulose, corn starch and potato starch; lubricants, e.g. silica, talc, stearic acid, magnesium or calcium stearate, and/or polyethylene glycols; binding agents, e.g. starches, arabic gums, gelatin, methylcellulose, carboxymethyl cellulose, polyvinyl pyrrolidone, disaggregating agents, e.g. a starch, alginic acid, alginates, sodium starch glycolate; effervescing mixtures; dyestuffs; sweeteners; wetting agents, such as, for instance, lecithin, polysorbates, laurylsulphates; and, in general, non-toxic and pharmacologically inactive substances used in pharmaceutical formulations. Said pharmaceutical preparations may be manufactured in known manner, for example, by means of mixing, granulating, tabletting, sugar-coating, or film-coating processes. The liquid dispersions for oral administration may be e.g. syrups, emulsions and suspensions. The syrups may contain as carrier, for example, saccharose or saccharose with glycerine and/or mannitol and/or sorbitol; in particular a syrup to be administered to diabetic patients can contain as carriers only products not metabolizable to glucose, or metabolizable in very small amount to glucose, such as, for example sorbitol.

The suspensions and the emulsions may contain as carrier, for example, a natural gum, agar, sodium alginate, pectin, methylcellulose, carboxymethylcellulose, or polyvinyl alcohol.

The suspensions or solutions for intramuscular injections may contain together with the active compound a pharmaceutically acceptable carrier, e.g. sterile isotonic water, olive oil, ethyl oleate, glycols, e.g. propylene glycol, and if desired, a suitable amount of lidocaine hydrochloride. The solutions for intravenous injections or infusions may contain as carrier, for example, sterile water or preferably they may be in the form of sterile, aqueous, isotonic saline solutions.

The suppositories may contain together with the active compound a pharmaceutically acceptable carrier, e.g. cocoa-butter, polyethylene glycol, a polyoxyethylene sorbitan fatty acid ester surfactant or lecithin.

The I.R. spectrum of the compounds was measured in solid phase (KBr) or Nujol solution or in a solution of a suitable solvent such as $CHCl_3$, using Perking-Elmer 125 spectrophotometer. The N.M.R. spectrum was measured preferably in solution of dimethyl sulphoxide-$d_6$ or of $CDCl_3$, using a 90 M-hertz Bruker HFX apparatus.

The $R_f$ values were determined by thin layer chromatography on ready-to-use silica gel plates of 0.25-mm coating thickness.

The following examples illustrate but do not limit the invention.

EXAMPLE 1

A solution of 3-bromo-7-methoxy-2,3-dihydro-4H-1-benzopyran-4-one (7 g), imidazole (8 g), and N,N-dimethylformamide (200 ml), was kept at 60° C. for 5 hours.

The solvent was evaporated under reduced pressure and the residue, taken up with $CH_2Cl_2$ (100 ml), washed with $H_2O$, was extracted with a solution of 8% HCl.

The acid solution, neutralized with $NaHCO_3$, extracted with $CH_2Cl_2$, dried and evaporated, gave 2 g of 3-(1-imidazolyl)-2,3-dihydro-7-methoxy-4H-1-benzopyran-4-one.

m.p. = 151°–155° C.

Elemental analysis: Found: C 62.99; H 4.87; N 11.28. Calculated for $C_{13}H_{12}N_2O_3$: C 63.93; H 4.95; N 11.47.

T.L.C. = eluent $CH_2Cl_2$: $CH_3OH$ = 180:20 $R_f$ = 0.33

| N.M.R ($CDCl_3$) δ p.p.m. |
|---|
| 3.91 (3H s O—$CH_3$) |
| 4.74 (2H m O—$CH_2$—CH—) |
| 5.06 (1H dd O—$CH_2$—CH—) |

| N.M.R (CDCl₃) δ p.p.m. |
|---|
| 6.54 (1H d CH₃O—C=CH—C—) with C=O and C= |
| 6.72 (1H dd CH₃O—C—CH=CH—) with C=O |
| 7.03 (1H s —N—CH=CH—N=) |
| 7.16 (1H s —N—CH=CH—N=) |
| 7.66 (1H s —N—CH=N—) |
| 7.92 (1H d CH₃O—C—CH=CH—) with C=O |

By proceeding analogously, the following compounds were prepared:

3-(1-imidazolyl)-2,3-dihydro-7-isopropyloxy-4H-1-benzopyran-4-one;
m.p.=80°–85° C.
Elemental analysis: Found: C 65.10; H 5.60; N 9.85.
Calculated for C₁₅H₁₆N₂O₃: C 66.16; H 5.92; N 10.28.
T.L.C.=eluent CH₂Cl₂: CH₃OH=180:20 R_f=0.5

| N.M.R. (CDCl₃) δ p.p.m. |
|---|
| 1.38 (6H d CH₃) |
| 4.67 (1H m CH₃—CH—CH₃) |
| 4.73 (2H dd O—CH₂—CH—) |
| 5.05 (1H dd O—CH₂—CH—) |
| 6.49–7.90 (6H m aromatics + imidazole) |

3-(1-imidazolyl)-2,3-dihydro-6-tert.butyl-7-hydroxy-4H-1-benzopyran-4-one;
m.p.=243°–245° C.
Elemental analysis: Found: C 66.88; H 6.21; N 9.52.
Calculated for C₁₆H₁₈N₂O₃: C 67.11; H 6.33; N 9.78.
T.L.C.=eluent CH₂Cl₂: CH₃OH=180:20 R_f=0.4

| N.M.R. (DMSO—d₆) δ p.p.m. |
|---|
| 1.35 (9H s CH₃) |
| 4.64 (1H dd O—CH—CH—) H |
| 4.80 (1H dd O—CH—CH—) H |
| 5.58 (1H dd O—CH₂—CH—) |
| 6.81 (1H s all. HO—C=CH—C—O—) with C=O |
| 6.98 (1H s all. —N—CH=CH) |
| 7.21 (1H s all. —N—CH=CH) |
| 7.66 (1H s all. (CH₃)₃C—C=CH—) |
| 7.73 (1H s all. —N—CH=N—) |

3-(1-imidazolyl)-2,3-dihydro-6-tert.butyl-4H-1-benzopyran-4-one;
m.p.=99°–100° C.
Elemental analysis: Found: C 70.58; H 6.64; N 10.26.
Calculated for C₁₆H₁₈N₂O₂: C 71.09; H 6.71; N 10.36.
T.L.C.=eluent CHCl₃: CH₃OH=180:20 Rf=0.31

| N.M.R. (CDCl₃) δ p.p.m. |
|---|
| 1.33 (9H, s CH₃) |
| 4.52 (2H m O—CH₂—CH—) |
| 5.11 (1H dd —O—CH₂—CH—) |
| 7.03 (1H s large —N—CH=CH—) |
| 7.06 (1H d —O—C—CH—) with C=O |
| 7.18 (1H s large —N—CH=CH—) |
| 7.66 (1H s large —N—CH=N—) |
| 7.68 (1H dd —O—C—CH=CH—) with C=O |
| 7.99 (1H d O=C—C—CH) |

3-(1-imidazolyl)-2,3-dihydro-7-tert.butyl-4H-1-benzopyran-4-one;
Elemental analysis: Found: C 70.21; H 6.61; N 10.28.
Calculated for C₁₆H₁₈N₂O₂: C 71.09; H 6.71; N 10.36.

| N.M.R. (CDCl₃) δ p.p.m. |
|---|
| 1.33 (9H s CH₃) |
| 4.5 (2H m —O—CH₂—CH—) |

| N.M.R. (CDCl₃) δ p.p.m. |
|---|
| 5.10 (1H dd —O—CH₂—CH—) |
| 7.0–7.95 (6H m aromatics + imidazole) |

3-(1-imidazolyl)-2,3-dihydro-6-hydroxy-7-tert.butyl-4H-1-benzopyran-4-one;

Elemental analysis: Found: C 67.1; H 6.39; N 9.4. Calculated for $C_{16}H_{18}N_2O_3$: C 67.11; H 6.33; N 9.78.

| I.R. (KBr) | |
|---|---|
| Stretching (O—H): | δ 3440 cm⁻¹; 3130 cm⁻¹ |
| Stretching (C—H) aliphatics: | δ 2960 cm⁻¹; 2930 cm⁻¹ |
| Stretching (C=O): | δ 1670 cm⁻¹ |
| Stretching (C—O) + bending (O—H): | δ 1400 cm⁻¹; 1240 cm⁻¹ |

3-(1-imidazolyl)-2,3-dihydro-4H-1-benzopyran-4-one m.p. 156°–158° C. (EtOH)

Analysis of the elements: Found: C 67.21; H 4.73; N 12.94. Theoretical for $C_{12}H_{10}N_2O_2$: C 67.27; H 4.71; N 13.08.

T.L.C. eluent CHCl₃:MeOH=170:30 Rf=0.50.

3-(1-imidazolyl)-2,3-dihydro-6-methoxy-4H-1-benzopyran-4-one; m.p. 150°–152° C. (EtOH 70%);

Analysis of the elements: found: C 63.69; H 4.95; N 11.27; theoretical for $C_{13}H_{12}N_2O_3$: C 63.9; H 4.95; N 11.47.

T.L.C. eluent: CHCl₃:MeOH=180:20 $R_f$=0.35

N.M.R.: (CDCl₃)δp.p.m. 3.85 (3H, s, —O—CH₃); 4.7 (2H, m, —O—CH₂—CH<); 5.04 (1H, m, —O—CH₂—CH<); 6.9–7.6 (6H, m, aromatics+imidazole).

3-(1-imidazolyl)-2,3-dihydro-6-phenoxy-4H-1-benzopyran-4-one;
3-(1-imidazolyl)-2,3-dihydro-6-hydroxy-S-n-propyl-4H-1-benzopyran-4-one;
3-(1-imidazolyl)-2,3-dihydro-5,7-diisopropyl-6-hydroxy-4H-1-benzopyran-4-one;
3-(1-imidazolyl)-2,3-dihydro-5,7-dibromo-6-hydroxy-4H-1-benzopyran-4-one;
3-(1-imidazolyl)-2,3-dihydro-6,8-ditert.butyl-4H-1-benzopyran-4-one;
3-(1-imidazolyl)-2,3-dihydro-5-hydroxy-6-tert.butyl-4H-1-benzopyran-4-one;
3-(1-imidazolyl)-2,3-dihydro-5-hydroxy-6-tert.butyl-8-isopropyl-4H-1-benzopyran-4-one;
3-(1-imidazolyl)-2,3-dihydro-6-amino-8-bromo-4H-1-benzopyran-4-one;
3-(1-imidazolyl)-2,3-dihydro-6-dimethylamino-8-bromo-4H-1-benzopyran-4-one;
3-(1-imidazolyl)-2,3-dihydro-6-chloro-7-hydroxy-4H-1-benzopyran-4-one;
3-(1-imidazolyl)-2,3-dihydro-6-isopropyl-7-hydroxy-4H-1-benzopyran-4-one;
3-(1-imidazolyl)-2,3-dihydro-6-tert.butyl-7-hydroxy-8-isopropyl-4H-1-benzopyran-4-one;
3-(1-imidazolyl)-2,3-dihydro-6,8-diisopropyl-7-hydroxy-4H-1-benzopyran-4-one;
3-(1-imidazolyl)-2,3-dihydro-6-hydroxy-8-chloro-4H-1-benzopyran-4-one;
3-(1-imidazolyl)-2,3-dihydro-6-hydroxy-8-isopropyl-4H-1-benzopyran-4-one;
3-(1-imidazolyl)-2,3-dihydro-5,7-ditert.butyl-6-hydroxy-4H-1-benzopyran-4-one.

EXAMPLE 2

A solution of 2-hydroxy-5-chloro-α-(1-imidazolyl)-acetophenone (2.4 g), paraformaldehyde (0.3 g) and acetic acid (45 ml) was refluxed for 30 minutes. The solvent was removed under reduced pressure, ethanol was added and the impurity traces were filtered off. The solvent was evaporated and the residue crystallized from MeOH:H₂O (75:25) affording 3-(1-imidazolyl)-2,3-dihydro-6-chloro-4H-1-benzopyran-4-one (2 g), m.p. 123°–125° C.

Analysis of the elements: Found: C 57.62; H 3.57; N 11.17. Theoretical for $C_{12}H_9N_2O_2Cl$: C 58.0; H 3.6; N 11.2.

T.L.C.: eluent: CHCl₃:MeOH:NH₄OH 32%=150:50:2
$R_f$=0.63

N.M.R. (CDCl₃)δp.p.m. 4.6–5.1 (2H, m, —O—CH₂—CH<) 5.84 (1H, m, —O—CH₂—CH<) 6.92–7.84 (6H, m, aromatics+imidazole).

Analogously, the following compounds were prepared:

3-(1-imidazolyl)-2,3-dihydro-7-chloro-4H-1-benzopyran-4-one;

Analysis of the elements: Found: C 57.12; H 3.48; N 11.15. Theoretical for $C_{12}H_9N_2O_2Cl$: C 58.0; H 3.6; N 11.2.

N.M.R. (CDCl₃)δp.p.m. 4.61–5.2 (2H m —O—CH₂—CH<) 5.86 (1H m —O—CH₂—CH<) 6.92–7.84 (6H m aromatics+imidazole)

3-(1-imidazolyl)-2,3-dihydro-6-methyl-4H-1-benzopyran-4-one; m.p. 105°–107° C.

Analysis of the elements: Found: C 67.72; H 5.23; N 11.98. Theoretical for $C_{13}H_{12}N_2O_2$: C 68.2; H 5.26; N 12.25.

I.R. (Nujol)
Stretching (C=O): 1690 cm⁻¹

3-(1-imidazolyl)-2,3-dihydro-6-trifluoromethyl-4H-1-benzopyran-4-one;
3-(1-imidazolyl)-2,3-dihydro-6-phenyl-4H-1-benzopyran-4-one;
3-(1-imidazolyl)-2,3-dihydro-7-phenyl-4H-1-benzopyran-4-one;
3-(1-imidazolyl)-2,3-dihydro-6,8-dichloro-4H-1-benzopyran-4-one;
3-(1-imidazolyl)-2,3-dihydro-5,7-dichloro-4H-1-benzopyran-4-one;
3-(1-imidazolyl)-2,3-dihydro-6-carboxy-8-n-propyl-4H-1-benzopyran-4-one;
3-(1-imidazolyl)-2,3-dihydro-6-carbamoyl-8-n-propyl-4H-1-benzopyran-4-one;
3-(1-imidazolyl)-2,3-dihydro-6-carbamoyl-4H-1-benzopyran-4-one;
3-(1-imidazolyl)-2,3-dihydro-6-carboxy-4H-1-benzopyran-4-one;
3-(1-imidazolyl)-2,3-dihydro-7-bromo-4H-1-benzopyran-4-one;

The 2-hydroxy-5-chloro-α-(1-imidazolyl)-acetophenone used above was prepared as follows: a solution of 2-hydroxy-5-chloro-α-bromo-acetophenone (7 g), imidazole (6 g) and N,N-dimethylformamide (50 ml), was heated to 40° C. for 2 hours. The solution was poured into ice-water, the solid was filtered off and taken up with NaOH. The basic solution, washed with CHCl₃, neutralized with HCl, extracted with CHCl₃, dried and evaporated to dryness gave 6 g of the above product, m.p. 201°-203° C. (Ethanol).

Analysis of the elements: Found: C 54.96; H 3.68; N 11.60; Cl 14.97; Theoretical for: $C_{11}H_9ClN_2O_2$: C 55.82; H 3.83; N 11.84; Cl 14.98.

EXAMPLE 3

A solution of 2-hydroxy-α-[1-(2-methyl)-imidazolyl]-acetophenone (2 g), paraformaldehyde (0.27 g) and acetic acid (15 ml) was refluxed for 5 hours. The solvent was removed under reduced pressure, methanol was added and the impurity traces were filtered off. Evaporation of the solvent gave 3-[1-(2-methyl)-imidazolyl]-2,3-dihydro-4H-1-benzopyran-4-one (1.8 g), m.p. 180°-182° C.

Analysis of the elements: Found: C 67.56; H 5.15; N 12.02; Theoretical for $C_{13}H_{12}N_2O_2$: C 68.40; H 5.30; N 12.27.

T.L.C.: eluent: $Et_2O$:MeOH:$NH_4OH$ 32%=190:10:0.5

$R_f$=0.4.

Analogously, the following compounds were prepared:

3-[1-(2-methyl)-imidazolyl]-2,3-dihydro-6-methoxy-4H-1-benzopyran-4-one, m.p. 190°-192° C.;

Analysis of the elements: Found: C 64.8; H 5.40; N 10.25; Theoretical for $C_{14}H_{14}N_2O_3$: C 65.1; H 5.46; N 10.84.

T.L.C.: eluent: $CHCl_3$:MeOH=170:30

$R_f$=0.61.

Analogously, the following compounds were prepared:

3-[1-(2,5-dimethyl)-imidazolyl]-2,3-dihydro-4H-1-benzopyran-4-one;

3-[1-(2-methyl)-imidazolyl]-2,3-dihydro-6-chloro-4H-1-benzopyran-4-one;

3-[1-(2,5-dimethyl)-imidazolyl]-2,3-dihydro-6-chloro-4H-1-benzopyran-4-one;

The 2-hydroxy-α-[1-(2-methyl)-imidazolyl]-acetophenone used above was prepared as follows: a solution of 2-hydroxy-α-bromoacetophenone (7.6 g), 2-methyl-imidazole (11.4 g) and N,N-dimethylformamide (60 ml) was heated to 40° C. for 10 hours. The solution was poured into ice-water. The solid was filtered off and taken up with NaOH. The basic solution was washed with $CHCl_3$, neutralized with HCl and extracted with $CHCl_3$. The extract, dried and evaporated to dryness gave 6.5 g of the above product m.p. 155°-160° C. (ethanol).

EXAMPLE 4

$NaBH_4$ (1 g) was added portionwise to a solution of 3-(1-imidazolyl)-2,3-dihydro-6-chloro-4H-1-benzopyran-4-one (2.7 g) in MeOH (70 ml) at 5°-10° C. The mixture, stirred at room temperature for 2 hours, added with water (300 ml), extracted with $CHCl_3$, dried and evaporated to dryness gave 3-(1-imidazolyl)-2,3-dihydro-6-chloro-4H-1-benzopyran-4-ol (cis and trans mixture; 1.9 g). The separation of the isomers was made by column chromatography of silica gel, eluent used: $CHCl_3$:MeOH:$NH_4OH$ 32%=170:30:1. A first a fraction was obtained consisting of cis-3-(1-imidazolyl)-2,3-dihydro-6-chloro-4H-1-benzopyran-4-ol (0.8 g) ($R_f$=0.44), m.p. 153°-160° C.

Analysis of the elements: Found: C 56.78; H 4.44; N 10.86; Cl 13.85; Theoretical for $C_{12}H_{11}N_2O_2Cl$: C 57.48; H 4.42; N 11.17; Cl 14.14.

| N.M.R. (pyridine) δ p.p.m. |
|---|
| 4.40-4.90 (3H, m,(O—CH$_2$—CH—N$\lessgtr$) |
| 5.18 (1H, d,(HO—CH—) |
| 6.96 (1H, d,(—CH=C—O—CH$_2$) |
| 7.30 (3H, m,(—N—CH=CH—N=; |
| Cl—C=CH—CH=C—O—) |
| 7.83 (1H, d,(Cl—C—CH=C—CH) OH |
| 8.03 (1H, s,(—N—CH=N—) J (HO—CH—CH—N$\lessgtr$) ~ 6.5 Hz |

Then a second fraction was obtained consisting of trans-3-(1-imidazolyl)-2,3-dihydro-6-chloro-4H-1-benzopyran-4-ol (1.1 g; $R_f$=0.39), m.p. 60°-65° C.

Analysis of the elements: Found: C 56.70; H 4.53; N 10.79; Cl 13.66; Theoretical for $C_{12}H_{11}N_2O_2Cl$: C 57.48; H 4.42; N 11.17; Cl 14.14.

| N.M.R. (pyridine) δ p.p.m. |
|---|
| 4.26-5.00 (3H, m, —O—CH$_2$—CH—N$\lessgtr$) |
| 5.19 (1H, d, HO—CH—) |
| 7.00 (1H, d, —CH=C—O—CH$_2$) |
| 7.31 (1H, d of d, Cl—C=CH—CH=C—O—) |
| 7.33 (1H, s, C—N—CH=CH—N=) |
| 7.46 (1H, s, C—N—CH=CH—N=) |
| 7.63 (1H, d, Cl—C—CH=C—CH—OH) |
| 8.12 (1H, s, —N—CH=N—) J (HO—CH—CH—N$\lessgtr$) ~ 2.2 Hz |

Analogously, the following compounds were prepared:

3-(1-imidazolyl)-2,3-dihydro-4H-1-benzopyran-4-ol, m.p. 126°-128° C.

Analysis of the elements: Found: C 66.67; H 5.73; N 12.8. Theoretical for $C_{12}H_{12}N_2O_2$: C 66.6; H 5.59; N 12.9.

T.L.C.: eluent CHCl$_3$:MeOH:NH$_4$OH 32% = 150:50:2
R$_f$ = 0.64

| N.M.R. (CDCl$_3$) δ p.p.m. |
| --- |
| 4.00–4.55 (3H, m, —O—CH$_2$—CH—) |
| 4.82 (1H, m, >CH—OH) |
| 6.07 (1H, s large, OH) |
| 6.50–7.50 (7H, m, aromatics + imidazole) |

3-(1-imidazolyl)-2,3-dihydro-6-methoxy-4H-1-benzopyran-4-ol, m.p. 171°–173° C. (EtOH);

Analysis of the elements: Found: C 63.34; H 5.77; N 11.22; Theoretical for $C_{13}H_{14}N_3O_3$: C 63.3; H 5.73; N 11.37;

T.L.C.: eluent: CHCl$_3$:MeOH:HCOOH 99% = 160:70:30
R$_f$ = 0.26

| N.M.R. (DMSO) δ p.p.m. |
| --- |
| 3.72 (3H, s, O—CH$_3$) |
| 4.2–5.00 (4H, m, —CH$_2$—CH—CH<) |
| 6.76–6.95 (3H, m, aromatics) |
| 6.94–7.16–7.64 (3H, imidazole) |

3-[1-(2-methyl)-imidazolyl]-2,3-dihydro-6-methoxy-4H-1-benzopyran-4-ol; m.p. 208°–210° C.

Analysis of the elements: Found: C 64.29; H 6.22; N 10.55; Theoretical for $C_{14}H_{16}N_2O_3$: C 64.60; H 6.19; N 10.76.

T.L.C.: eluent: CHCl$_3$:MeOH = 170:30
R$_f$ = 0.25

| N.M.R. (DMSO) δ p.p.m. |
| --- |
| 2.40 (3H, s, H$_3$C—C=N—) |
| 3.98 (3H, s, O—CH$_3$) |
| 4.20–4.80 (3H, m, HO—CH—CH—CH$_2$—O—) |
| 4.90 (1H, d large, HO—CH—) |
| 6.08 (1H, s, —OH) |
| 6.68–7.20 (5H, m, aromatics + |

| N.M.R. (DMSO) δ p.p.m. |
| --- |
| imidazole) J (HO—CH—CH—N<) ~ 3.5 Hz |

3-[1-(2-methyl)-imidazolyl]-2,3-dihydro-4H-1-benzopyran-4-ol, m.p. 170° C. (dec.)

Analysis of the elements: Found C 66.92; H 6.20; N 11.73; Theoretical for $C_{13}H_{14}N_2O_2$: C 67.8; H 6.12; N 12.1

T.L.C.: eluent: CHCl$_3$:MeOH = 170:30
R$_f$ = 0.27

3-(1-imidazolyl)-2,3-dihydro-7-methoxy-4H-1-benzopyran-4-ol;

Elemental analysis Found: C 63.34; H 5.77; N 11.22; Theoretical for $C_{13}H_{14}N_3O_3$: C 63.3; H 5.73; N 11.37.

| N.M.R. (DMSO) δ p.p.m. |
| --- |
| 3.73 (3H, s, OCH$_3$) |
| 4.15–5.1 (4H, m, —CH$_2$—CH—CH<) |
| 6.70–7.65 (6H, m, aromatics + imidazole) |

3-(1-imidazolyl)-2,3-dihydro-6-tert.butyl-7-hydroxy-4H-1-benzopyran-4-ol;
3-(1-imidazolyl)-2,3-dihydro-6-bromo-7-hydroxy-4H-1-benzopyran-4-ol;
3-(1-imidazolyl)-2,3-dihydro-6-tert.butyl-4H-1-benzopyran-4-ol;
3-(1-imidazolyl)-2,3-dihydro-6,8-dibromo-7-hydroxy-4H-1-benzopyran-4-ol;
3-(1-imidazolyl)-2,3-dihydro-6-hydroxy-8-bromo-4H-1-benzopyran-4-ol;
3-(1-imidazolyl)-2,3-dihydro-6-bromo-4H-1-benzopyran-4-ol;
3-(1-imidazolyl)-2,3-dihydro-6-phenyl-4H-1-benzopyran-4-ol;
3-(1-imidazolyl)-2,3-dihydro-7-chloro-4H-1-benzopyran-4-ol;
3-(1-imidazolyl)-2,3-dihydro-6,8-dichloro-4H-1-benzopyran-4-ol;
3-(1-imidazolyl)-2,3-dihydro-6,8-dibromo-4H-1-benzopyran-4-ol.

EXAMPLE 5

A solution of CH$_3$I (0.66 g) in anhydrous tetrahydrofurane (15 ml) was added to metallic anhydrous magnesium. A small crystal of iodine was added to the mixture, which was stirred at room temperature for one hour and then cooled in a cold water bath.

A solution of 3-(1-imidazolyl)-2,3-dihydro-6-chloro-4H-1-benzopyran-4-one (0.5 g) in anhydrous tetrahydrofurane (20 ml) was added to the reaction mixture, which was refluxed moderately for 30 minutes and then for 1 hour on a water bath. The mixture was cooled, poured into a mixture of crushed ice and water (100 ml) and extracted with CHCl$_3$ (100 ml). The organic layer, dried on anhydrous Na$_2$SO$_4$ and evaporated to dryness under vacuum afforded
3-(1-imidazolyl)-2,3-dihydro-4-methyl-6-chlorobenzopyran-4-ol (0.3 g);

Analysis of the elements: Found: C 58.1; H 4.66; N 10.40; Cl 13.00. Theoretical for $C_{13}H_{13}ClN_2O_2$: C 59.0; H 4.91; N 10.59; Cl 13.38.

N.M.R. δ p.p.m. 1.4 (3H s CH$_3$) 4.20-4.80 (3H m O—CH$_2$—CH—) 7.00-8.10 (6H m aromatics-+imidazole)

EXAMPLE 6

Br$_2$ (1.7 g) was added dropwise to a solution of 3-(1-imidazolyl)-2,3-dihydro-4H-1-benzopyran-4-one (1 g) and AlCl$_3$ (3.5 g) in 40 ml of CH$_2$Cl$_2$. The solution was refluxed for 4 hours. Then water was added giving after acidification with HCl and filtration, 3-(1-imidazolyl)-2,3-dihydro-6,8-dibromo-4H-1-benzopyran-4-one hydrochloride (1 g), m.p. 280° C. (dec.)

Analysis of the elements: Found: C 34.88; H 2.19; N 6.73; Br 38.30; Cl 8.50. Theoretical for $C_{12}H_8Br_2N_2O_2 \cdot HCl$: C 35.28; H 2.22; N 6.86; Br 39.12; Cl 8.68.

T.L.C.: eluent: CHCl$_3$:MeOH=170:30
R$_f$=0.45

| N.M.R. (CF$_3$COOD) δ p.p.m. |
| --- |
| 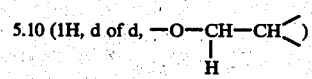 |
| 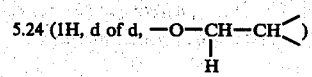 |
| 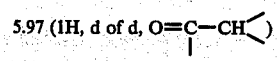 |
| 7.70 (2H, s large, —N—CH=CH—N—) |
|  |
| 9.15 (1H, s large, —N—CH=N—) |
| 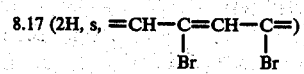 |
| 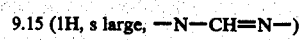 |
| I.R. (KBr): ν(NH⊕) 3160-3140 cm$^{-1}$; 2800-2740-2620 cm$^{-1}$; |
| ν(C—H) arom. 3070-3020 cm$^{-1}$; |
| ν(C=O) 1705 cm$^{-1}$ |
| ν(C=C) ⎫ |
| ν(C=N) ⎬ 1585-1565-1540 cm$^{-1}$ |
| ν(C—H) 1,2,3,5-substituted benzene ring group |
| ν(C—Br) 645 cm$^{-1}$ |

Analogously, the following compounds were prepared:

3-(1-imidazolyl)-2,3-dihydro-6-bromo-4H-1-benzopyran-4-one hydrochloride; m.p. 260°-265° C. (dec.)
Analysis of the elements: Found: C 43.51; H 2.91; N 8.21; Br 23.96; Cl 10.67; Theoretical for $C_{12}H_9BrN_2O_2 \cdot HCl$: C 43.73; H 3.06; N8.50; Br 24.24; Cl 10.75;

T.L.C.: eluent: CHCl$_3$:CH$_3$OH (180:20)
R$_f$=0.39

| N.M.R. (CF$_3$COOD) δ p.p.m. |
| --- |
| 5.07 (2H, m, —O—CH$_2$—CH<) |
| 5.87 (1H, d of d, O=C—CH<) |
| 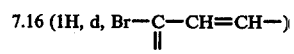 |
| 7.65 (2H, s large, —N—CH=CH—N—) |
| 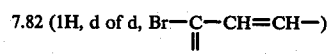 |
|  |
| 9.07 (1H, s large, —N—CH=N—) |
| I.R. (KBr): ν(NH⊕) 3100-2600 cm$^{-1}$ |
| ν(C=O) 1705 cm$^{-1}$ |
| ν(C=C) ⎫ |
| ⎬ 1595-1565-1470 cm$^{-1}$ |
| ν(C=N) ⎭ |
| ν(C—O) ether. 1270 cm$^{-1}$ |
| ν(C—Br) 645 cm$^{-1}$ |

3-(1-imidazolyl)-2,3-dihydro-6-tert.butyl-8-bromo-4H-1-benzopyran-4-one, hydrochloride;
Elemental analysis Found: C 49.1; H 4.57; N 7.15; Br 21.00. Calculated for $C_{16}H_{17}BrN_2O_2HCl$: C 49.81; H 4.67; N 7.26; Br 20.75.

| N.M.R. (DMSO—d6) δ p.p.m. |
| --- |
| 1.33 (9H, s, CH$_3$) |
| 4.95-5.25 (2H, m, —O—CH$_2$—CH<) |
| 6.35 (1H, dd, —O—CH$_2$—CH—) |
| 7.71-7.90 (4H, m, aromatics + imidazole) |
| 9.30 (1H, s large, —N—CH=N—) |

3-(1-imidazolyl)-2,3-dihydro-6-methyl-8-bromo-4H-1-benzopyran-4-one hydrochloride;
m.p.=270°-2° C. (dec).
Elemental analysis Found: C 46.1; H 3.60; N 8.06; Br 22.80; Cl 10.23 Calculated for $C_{13}H_{11}N_2O_2Br \cdot HCl$: C 45.44; H 3.52; N 8.15 Br 23.25; Cl 10.32
T.L.C.=eluent CH$_3$Cl: CH$_3$OH=180:20 R$_f$=0.4

| N.M.R. (DMSO) δ p.p.m. |
| --- |
| 2.34 (s 3H CH$_3$) |
| 4.90-5.30 (m 2H —O—CH$_2$—CH—) |

-continued

| N.M.R. (DMSO) δ p.p.m. |
|---|
| 6.37 (dd 1H —O—CH$_2$—CH—) |
| 7.73 (d 1H CH$_3$—C—CH=C—Br) |
| 7.82 (s large 1H —N—CH=CH—N=) |
| 7.87 (s large 1H —N—CH=CH—N=) |
| 7.92 (d 1H CH$_3$—C=CH—C—) |
| 9.32 (s large 1H —N—CH=N—) |

3-(1-imidazolyl)-2,3-dihydro-5,8-dibromo-6-hydroxy-4H-1-benzopyran-4-one hydrochloride;
3-(1-imidazolyl)-2,3-dihydro-6-carbamoyl-8-bromo-4H-1-benzopyran-4-one hydrochloride;
3-(1-imidazolyl)-2,3-dihydro-6-carboxy-8-bromo-4H-1-benzopyran-4-one hydrochloride;
3-(1-imidazolyl)-2,3-dihydro-6-tert.butyl-7-hydroxy-8-bromo-4H-1-benzopyran-4-one hydrochloride;
3-(1-imidazolyl)-2,3-dihydro-6-bromo-7-hydroxy-4H-1-benzopyran-4-one hydrochloride;
3-(1-imidazolyl)-2,3-dihydro-6,8-dibromo-7-hydroxy-4H-1-benzopyran-4-one hydrochloride;
3-(1-imidazolyl)-2,3-dihydro-6-hydroxy-8-bromo-4H-1-benzopyran-4-one hydrochloride;

EXAMPLE 7

3-(1-imidazolyl)-2,3-dihydro-7-methoxy-4H-1-benzopyran-4-one (1 g) was refluxed with 48% hydrobromic acid (60 ml) for 7 hours.

The solution was cooled in ice. The solid was filtered off, washed with ice-water and dried, giving 3-(1-imidazolyl)-2,3-dihydro-7-hydroxy-4H-1-benzopyran-4-one hydrobromide;

m.p.=318° C. (dec)

Elemental analysis Found: C 46.10; H 3.48; N 8.92. Calculated for C$_{12}$H$_{10}$N$_2$O$_3$.HBr=C 46.32; H 3.56; N 9.00.

T.L.C.=eluent CH$_2$Cl$_2$: CH$_3$OH=180:20 R$_f$=0.2

| N.M.R. (DMSO—d$_6$) δ p.p.m. |
|---|
| 4.93 (m 2H —O—CH$_2$—CH—) |
| 6.15 (dd 1H —O—CH$_2$—CH—) |
| 6.51 (d 1H HO—C=CH—C—O—) |
| 6.69 (dd 1H HO—C—CH=CH—) |

-continued

| N.M.R. (DMSO—d$_6$) δ p.p.m. |
|---|
| 7.78 (d 1H HO—C—CH=CH—) |
| 7.86 (s large 2H —N—CH=CH—N=) |
| 9.35 (s large 1H —N—CH=N—) |

By proceeding analogously the following compound was obtained:
3-(1-imidazolyl)-2,3-dihydro-6-hydroxy-4H-1-benzopyran-4-one hydrobromide;

EXAMPLE 8

3-(1-imidazolyl)-2,3-dihydro-7-bromo-4H-1-benzopyran-4-one was treated with a stoichiometric amount of hydrogen chloride, to give 3-(1-imidazolyl)-2,3-dihydro-7-bromo-4-H-1-benzopyran-4-one hydrochloride;

Elemental analysis Found: C 43.45; H 3.00; N 8.35; Br 24.10. Calculated for C$_{12}$H$_9$BrN$_2$O$_2$.HCl: C 43.73; H 3.06; N 8.50; Br 24.24.

N.M.R. (CF$_3$COOD) δ p.p.m. 5.08 (2H m —O—CH$_2$—CH<) 5.88 (1H m O—CH$_2$—CH<) 7.10–9.08 (6H m aromatics+imidazole)

By proceeding similarly the hydrochloride derivatives of all the compounds, obtained in Examples 1 and 2, were obtained.

EXAMPLE 9

3-(1-imidazolyl)-2,3-dihydro-6-hydroxy-4H-1-benzopyran-4-one hydrobromide, treated with the stoichiometric amount of NaHCO$_3$, gave 3-(1-imidazolyl)-2,3-dihydro-6-hydroxy-4H-1-benzopyran-4-one;

m.p.=245°–7° C. (CH$_3$OH)

Found: C 61.2; H 4.22; N 11.7; Calculated for C$_{12}$H$_{10}$N$_2$O$_3$: C 62.6; H 4.38; N 12.1.

By proceeding analogously the following compounds were obtained:
3-(1-imidazolyl)-2,3-dihydro-6,8-dibromo-7-hydroxy-4H-1-benzopyran-4-one;

Elemental analysis Found: C 36.6; H 2.10; N 7.8; Br 40.29. Calculated for C$_{12}$H$_8$Br$_2$N$_2$O$_3$: C 37.14; H 2.07; N 7.21; Br 41.18.

N.M.R. δp.p.m. 5.00 (2H m O—CH$_2$—CH—)5.95 (1H m O—CH$_2$—CH—) 6.70–7.8 (4H m aromatic-+imidazole)

3-(1-imidazolyl)-2,3-dihydro-6-hydroxy-8-bromo-4H-1-benzopyran-4-one;

Elemental analysis Found: C 46.12; H 2.85; N 8.95; Br 25.75. Calculated for C$_{12}$H$_9$N$_2$O$_3$Br: C 46.62; H 2.93; N 9.06; Br 25.85.

N.M.R. δ p.p.m. 4.6–5.2 (2H m O—CH$_2$—CH—) 5.95 (1H m O—CH$_2$—CH) 6.80–7.85 (5H m aromatic-+imidazole)

3-(1-imidazolyl)-2,3-dihydro-6,8-dibromo-4H-1-benzopyran-4-one;
3-(1-imidazolyl)-2,3-dihydro-6-bromo-4H-1-benzopyran-4-one;
3-(1-imidazolyl)-2,3-dihydro-6-tert.butyl-8-bromo-4-1-benzopyran-4-one;
3-(1-imidazolyl)-2,3-dihydro-6-methyl-8-bromo-4H-1-benzopyran-4-one;
3-(1-imidazolyl)-2,3-dihydro-5,8-dibromo-6-hydroxy-4H-1-benzopyran-4-one;

3-(1-imidazolyl)-2,3-dihydro-6-carbamoyl-8-bromo-4H-1-benzopyran-4-one;

3-(1-imidazolyl)-2,3-dihydro-6-carboxy-8-bromo-4H-1-benzopyran-4-one;

3-(1-imidazolyl)-2,3-dihydro-6-tert.butyl-7-hydroxy-8-bromo-4H-1-benzopyran-4-one;

3-(1-imidazolyl)-2,3-dihydro-6-bromo-7-hydroxy-4H-1-benzopyran-4-one;

3-(1-imidazolyl)-2,3-dihydro-7-hydroxy-4-1-benzopyran-4-one.

Formulation Examples

Formulation 1: Tablet

Tablets, each weighing 300 mg and containing 100 mg of the active substance are manufactured as follows:

| Composition (for 10,000 tablets) | |
|---|---|
| 3-(1-imidazolyl)-2,3-dihydro-6-tert.butyl-7-hydroxy-4H-1-benzopyran-4-one | 1000 g |
| Lactose | 1420 g |
| Corn starch | 475 g |
| Talc powder | 75 g |
| Magnesium stearate | 30 g |

3-(1-imidazolyl)-2,3-dihydro-6-tert.butyl-7-hydroxy-4H-1-benzopyran-4-one, lactose, and a half of the corn starch are mixed; the mixture is then forced through a sieve of 0.5 mm openings. Corn starch (18 g) is suspended in warm water (180 ml). The resulting paste is used to granulate the powder. The granules are dried, comminuted on a sieve of sieve size 1.4 mm, then the remaining quantity of starch, talc and magnesium stearate is added, carefully mixed, and processed into tablets using punches of 10 mm diameter.

Formulation 2: intramuscular injection

An injectable pharmaceutical composition was manufactured by dissolving 50–100 mg of 3-(1-imidazolyl)-2,3-dihydro-6-tert.butyl-7-hydroxy-4H-1-benzopyran-4-one hydrochloride in sterile water or sterile aqueous normal saline solution (1–2 ml).

Formulation 3: Capsule with the usual methods of pharmaceutical technique, preparation was made of capsules having the following composition:

| 3-(1-imidazolyl)-2,3-dihydro-6-tert.butyl-7-hydroxy-4H-1-benzopyran-4-one | 50 mg |
|---|---|
| Lactose | 298 mg |
| Corn starch | 50 mg |
| Magnesium stearate | 2 mg |

Formulation 4: Suppository with the usual methods of pharmaceutical technique, preparation was made of suppositories having the following composition:

| 3-(1-imidazolyl)-2,3-dihydro-6-tert.butyl-7-hydroxy-4H-1-benzopyran-4-one | 0.05 g |
|---|---|
| Lecithin | 0.07 g |
| Cacao butter | 0.88 g |

Formulation 5: Capsule with the usual methods of pharmaceutical technique, preparation was made of capsules having the following composition:

| 3-(1-imidazolyl)-2,3-dihydro-6-chloro-4H-1-benzopyran-4-one | 50 mg |
|---|---|
| Lactose | 298 mg |
| Corn starch | 50 mg |
| Magnesium stearate | 2 mg |

Formulation 6: Suppository with the usual methods of pharmaceutical technique, preparation was made of suppositories having the following composition:

| 3-(1-imidazolyl)-2,3-dihydro-6,8-dibromo-4H-1-benzopyran-4-one | 0.05 g |
|---|---|
| Lecithin | 0.07 g |
| Cacao butter | 0.88 g |

We claim:

1. Compounds having the general formula (I)

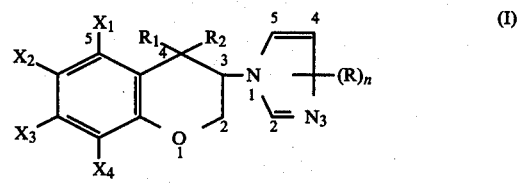

wherein

R is $C_1-C_6$ alkyl;

n is 0, 1, 2 or 3 one of $R_1$ and $R_2$ is hydroxy and the other is hydrogen or $C_1-C_6$ alkyl, or $R_1$ and $R_2$, taken together, form an oxo group;

each of $X_1$, $X_2$, $X_3$ and $X_4$, which may be the same or different, is hydrogen; halogen; hydroxy; $-NO_2$; $-CN$; $C_1-C_6$ alkyl; $C_1-C_6$ alkoxy; trihalo-$C_1-C_6$ alkyl; $-SR'$ or $-COOR'$, $R'$ being hydrogen or $C_1-C_6$ alkyl;

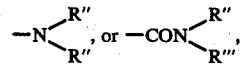

each of $R''$ and $R'''$, which may be the same or different, being hydrogen or $C_1-C_6$ alkyl; or one of $X_1$, $X_2$, $X_3$ and $X_4$ is phenyl, phenylthio, phenoxy or benzyl, the phenyl, phenylthio, phenoxy and benzyl groups being unsubstituted or substituted by halogen, $C_1-C_6$ alkyl, $C_{1-6}$ alkoxy, or $-SR'$, wherein $R'$ is as defined above, and the others are as defined above; or any two adjacent $X_1$, $X_2$, $X_3$ and $X_4$ groups, taken together, complete a saturated or unsaturated 6-membered carbocyclic ring fused to the benzene ring shown in formula (I), the carbocyclic ring being unsubstituted or substituted by one or more groups selected from halogen, $C_1-C_6$ alkyl, $C_{1-6}$ haloalkyl, $C_1-C_6$ alkoxy or $-SR'$, wherein $R'$ is as defined above, and any groups $X_1$ to $X_4$ not participating in the completion of such a fused ring are as defined above, or a pharmaceutically acceptable salt thereof.

2. A compound having formula (I) wherein n is zero, one of $R_1$ and $R_2$ is hydrogen and the other is hydroxy, or $R_1$ and $R_2$, taken together, form an oxo group, and wherein $X_1$, $X_2$, $X_3$ and $X_4$ are, independently, hydrogen, halogen, hydroxy, carboxy, trifluoromethyl, $C_1$–$C_4$ alkylthio, $C_1$–$C_4$ $C_1$–$C_4$ alkoxy, carbamoyl or

wherein R'' and R''' are as defined above, or one of $X_1$, $X_2$, $X_3$ and $X_4$ is phenyl, phenylthio, phenoxy or benzyl, the phenyl, phenylthio, phenoxy and benzyl groups being unsubstituted or substituted by halogen, $C_1$–$C_4$ alkyl, $C_1$–$C_4$ alkylthio or $C_1$–$C_4$ alkoxy, and the others are independently, hydrogen, halogen, $C_1$–$C_4$ alkyl, $C_1$–$C_4$ alkylthio or $C_1$–$C_4$ alkoxy, or a pharmaceutically acceptable salt thereof.

3. A compound having the formula (I) reported above in claim 1, wherein n is zero, one of $R_1$ and $R_2$ is hydroxy and the other is hydrogen, or $R_1$ and $R_2$, taken together, form an oxo group and wherein $X_1$, $X_2$, $X_3$ and $X_4$ are, independently, hydrogen, halogen, trifluoromethyl, $C_1$–$C_4$ alkylthio, $C_1$–$C_4$ alkyl, $C_1$–$C_4$ alkoxy, hydroxy, carboxy, carbamoyl or

where R'' and R''' are as defined in claim 1, or a pharmaceutically salt thereof.

4. 3-(1-imidazolyl)-2,3-dihydro-4H-1-benzopyran-4-one, as claimed in claim 1.

5. 3-(1-imidazolyl)-2,3-dihydro-6-methyl-4H-1-benzopyran-4-one, as claimed in claim 1.

6. 3-(1-imidazolyl)-2,3-dihydro-6-chloro-4H-1-benzopyran-4-one, as claimed in claim 1.

7. 3-(1-imidazolyl)-2,3-dihydro-6-bromo-4H-1-benzopyran-4-one, as claimed in claim 1.

8. 3-(1-imidazolyl)-2,3-dihydro-6-trifluoromethyl-4H-1-benzopyran-4-one, as claimed in claim 1.

9. 3-(1-imidazolyl)-2,3-dihydro-6-methoxy-4H-1-benzopyran-4-one, as claimed in claim 1.

10. 3-(1-imidazolyl)-2,3-dihydro-6-phenyl-4H-1-benzopyran-4-one, as claimed in claim 1.

11. 3-(1-imidazolyl)-2,3-dihydro-6-phenoxy-4H-1-benzopyran-4-one, as claimed in claim 1.

12. 3-(1-imidazolyl)-2,3-dihydro-7-chloro-4H-1-benzopyran-4-one, as claimed in claim 1.

13. 3-(1-imidazolyl)-2,3-dihydro-7-phenyl-4H-1-benzopyran-4-one, as claimed in claim 1.

14. 3-(1-imidazolyl)-2,3-dihydro-6,8-dichloro-4H-1-benzopyran-4-one, as claimed in claim 1.

15. 3-(1-imidazolyl)-2,3-dihydro-6,8-dibromo-4H-1-benzopyran-4-one, as claimed in claim 1.

16. 3-(1-imidazolyl)-2,3-dihydro-5,7-dichloro-4H-1-benzopyran-4-one, as claimed in claim 1.

17. 3-(1-imidazolyl)-2,3-dihydro-7-methoxy-4H-1-benzopyran-4-one, as claimed in claim 1.

18. 3-(1-imidazolyl)-2,3-dihydro-6-hydroxy-8-n-propyl-4H-1benzopyran-4-one, as claimed in claim 1.

19. 3-(1-imidazolyl)-2,3-dihydro-7-isopropyloxy-4H-1-benzopyran-4-one, as claimed in claim 1.

20. 3-(1-imidazolyl)-2,3-dihydro-5,7-diisopropyl-6-hydroxy-4H-1-benzopyran-4-one, as claimed in claim 1.

21. 3-(1-imidazolyl)-2,3-dihydro-7-hydroxy-4H-1-benzopyran-4-one, as claimed in claim 1.

22. 3-(1-imidazolyl)-2,3-dihydro-6-bromo-7-hydroxy-4H-1-benzopyran-4-one, as claimed in claim 1.

23. 3-(1-imidazolyl)-2,3-dihydro-6,8-dibromo-7-hydroxy-4H-1-benzopyran-4-one, as claimed in claim 1.

24. 3-(1-imidazolyl)-2,3-dihydro-6-chloro-7-hydroxy-4H-1-benzopyran-4-one, as claimed in claim 1.

25. 3-(1-imidazolyl)-2,3-dihydro-6-tert.butyl-7-hydroxy-4H-1-benzopyran-4-one, as claimed in claim 1.

26. 3-(1-imidazolyl)-2,3-dihydro-6-isopropyl-7-hydroxy-4H-1-benzopyran-4-one, as claimed in claim 1.

27. 3-(1-imidazolyl)-2,3-dihydro-6-tert.butyl-7-hydroxy-8-isopropyl-4H-1-benzopyran-4-one, as claimed in claim 1.

28. 3-(1-imidazolyl)-2,3-dihydro-6,8-diisopropyl-7-hydroxy-4H-1-benzopyran-4-one, as claimed in claim 1.

29. 3-(1-imidazolyl)-2,3-dihydro-7-bromo-4H-1-benzopyran-4-one, as claimed in claim 1.

30. 3-(1-imidazolyl)-2,3-dihydro-5,7-dibromo-6-hydroxy-4H-1-benzopyran-4-one, as claimed in claim 1.

31. 3-(1-imidazolyl)-2,3-dihydro-6-hydroxy-4H-1-benzopyran-4-one, as claimed in claim 1.

32. 3-(1-imidazolyl)-2,3-dihydro-6-hydroxy-8-bromo-4H-1-benzopyran-4-one, as claimed in claim 1.

33. 3-(1-imidazolyl)-2,3-dihydro-6-hydroxy-8-chloro-4H-1-benzopyran-4-one, as claimed in claim 1.

34. 3-(1-imidazolyl)-2,3-dihydro-6-hydroxy-8-isopropyl-4H-1-benzopyran-4-one, as claimed in claim 1.

35. 3-(1-imidazolyl)-2,3-dihydro-5,8-dibromo-6-hydroxy-4H-1-benzopyran-4-one, as claimed in claim 1.

36. 3-(1-imidazolyl)-2,3-dihydro-5,7-ditert.butyl-6-hydroxy-4H-1-benzopyran-4-one, as claimed in claim 1.

37. 3-(1-imidazolyl)-2,3-dihydro-5-hydroxy-6-tert.butyl-4H-1-benzopyran-4-one, as claimed in claim 1.

38. 3-(1-imidazolyl)-2,3-dihydro-5-hydroxy-6-tert.butyl-8-isopropyl-4H-1-benzopyran-4-one, as claimed in claim 1.

39. 3-(1-imidazolyl)-2,3-dihydro-6-methyl-8-bromo-4H-1-benzopyran-4-one, as claimed in claim 1.

40. 3-(1-imidazolyl)-2,3-dihydro-6-tert.butyl-7-hydroxy-8-bromo-4H-1-benzopyran-4-one, as claimed in claim 1.

41. 3-(1-imidazolyl)-2,3-dihydro-6-amino-8-bromo-4H-1-benzopyran-4-one, as claimed in claim 1.

42. 3-(1-imidazolyl)-2,3-dihydro-6-dimethylamino-8-bromo-4H-1-benzopyran-4-one, as claimed in claim 1.

43. 3-(1-imidazolyl)-2,3-dihydro-6-tert.butyl-4H-1-benzopyran-4-one, as claimed in claim 1.

44. 3-(1-imidazolyl)-2,3-dihydro-6-carbamoyl-4H-1-benzopyran-4-one, as claimed in claim 1.

45. 3-(1-imidazolyl)-2,3-dihydro-6-carboxy-4H-1-benzopyran-4-one, as claimed in claim 1.

46. 3-(1-imidazolyl)-2,3-dihydro-6-carbamoyl-8-bromo-4H-1-benzopyran-4-one, as claimed in claim 1.

47. 3-(1-imidazolyl)-2,3-dihydro-6-carboxy-8-bromo-4H-1-benzopyran-4-one, as claimed in claim 1.

48. 3-(1-imidazolyl)-2,3-dihydro-6-carboxy-8-n-propyl-4H-1-benzopyran-4-one, as claimed in claim 1.

49. 3-(1-imidazolyl)-2,3-dihydro-6-carbamoyl-8-n-propyl-4H-1-benzopyran-4-one, as claimed in claim 1.

50. 3-(1-imidazolyl)-2,3-dihydro-7-tert.butyl-4H-1-benzopyran-4-one, as claimed in claim 1.

51. 3-(1-imidazolyl)-2,3dihydro-6,8-ditert.butyl-4H-1-benzopyran-4-one, as claimed in claim 1.

52. 3-(1-imidazolyl)-2,3-dihydro-6-hydroxy-7-tert.butyl-4H-1-benzopyran-4-one, as claimed in claim 1.

53. 3-(1-imidazolyl)-2,3-dihydro-6-tert.butyl-8-bromo-4H-1-benzopyran-4-one, as claimed in claim 1.

54. A pharmaceutically acceptable salt of each of the compounds of claims 4 to 53.

55. A pharmaceutically acceptable salt of each of the compounds of claim 4 to 53, wherein said salt is the hydrochloride.

56. A pharmaceutically acceptable salt of each of the compounds of claims 4 to 53, wherein said salt is the hydrobromide.

57. 3-(1-imidazolyl)-2,3-dihydro-6,8-dichloro-4H-1-benzopyran-4-ol, as claimed in claim 1.

58. 3-(1-imidazolyl)-2,3-dihydro-6,8-dibromo-4H-1-benzopyran-4-ol, as claimed in claim 1.

59. 3-(1-imidazolyl)-2,3-dihydro-6-tert.butyl-7-hydroxy-4H-1-benzopyran-4-ol, as claimed in claim 1.

60. 3-(1-imidazolyl)-2,3-dihydro-6-bromo-7-hydroxy-4H-1-benzopyran-4-ol, as claimed in claim 1.

61. 3-(1-imidazolyl)-2,3-dihydro-6-tert.butyl-4H-1-benzopyran-4-ol, as claimed in claim 1.

62. 3-(1-imidazolyl)-2,3-dihydro-6,8-dibromo-7-hydroxy-4H-1-benzopyran-4-ol, as claimed in claim 1.

63. 3-(1-imidazolyl)-2,3-dihydro-6-hydroxy-8-bromo-4H-1-benzopyran-4-ol, as claimed in claim 1.

64. 3-(1-imidazolyl)-2,3-dihydro-7-methoxy-4H-1-benzopyran-4-ol, as claimed in claim 1.

65. 3-(1-imidazolyl)-2,3-dihydro-4H-1-benzopyran-4-ol, as claimed in claim 1.

66. 3-(1-imidazolyl)-2,3-dihydro-6-chloro-4H-1-benzopyran-4-ol, as claimed in claim 1.

67. 3-(1-imidazolyl)-2,3-dihydro-6-bromo-4H-1-benzopyran-4-ol, as claimed in claim 1.

68. 3-(1-imidazolyl)-2,3-dihydro-6-methoxy-4H-1-benzopyran-4-ol, as claimed in claim 1.

69. 3-(1-imidazolyl)-2,3-dihydro-6-phenyl-4H-1-benzopyran-4-ol, as claimed in claim 1.

70. 3-(1-imidazolyl)-2,3-dihydro-7-chloro-4H-1-benzopyran-4-ol, as claimed in claim 1.

71. A compound according to any one of claims 57 to 70, where the compound is a cis or a trans isomer or a mixture thereof.

72. A pharmaceutically acceptable salt of each of the compounds of claims 57 to 71.

73. A method of increasing total serum HDL cholestrol in a patient in need of such treatment, and/or of increasing the ratio between α-lipoprotein and β-lipoprotein total cholestrol in a patient in need of such treatment, and/or of reducing total serum cholesterol or serum triglycerides in a patient in need of said treatment, said method comprising administering to said patient an effective amount therefor of a compound of claim 1.

74. A composition for use in administration to human patients to inhibit blood platelet aggregation, to increase HDL cholesterol concentration in blood and/or the ratio between α-lipoprotein and β-lipoprotein cholesterol, or to reduce cholesterol or triglyceride level of the blood, said composition comprising an effective amount of a compound of claim 1 and a pharmaceutically acceptable carrier therefor.

75. A method of inhibiting blood platelet aggregation in a patient in need of such treatment, said method comprising administering to said patient an effective platelet aggregation inhibiting amount of a compound of claim 1.

76. A method of treating thrombosis in a patient in need of such treatment, said method comprising administering to said patient an effective antithrombotic amount of a compound of claim 1.

* * * * *

UNITED STATES PATENT AND TRADEMARK OFFICE
CERTIFICATE OF CORRECTION

PATENT NO. : 4,342,775
DATED : August 3, 1982
INVENTOR(S) : PAOLO COZZI et al

It is certified that error appears in the above—identified patent and that said Letters Patent is hereby corrected as shown below:

Column 19, line 41, after "hydroxy-" change "S" to --8--.

Column 31, line 6, after "$C_1-C_4$" (second occurrence) insert --alkyl,--.

Signed and Sealed this

Thirtieth Day of October 1984

[SEAL]

Attest:

GERALD J. MOSSINGHOFF

*Attesting Officer*  *Commissioner of Patents and Trademarks*